(12) United States Patent
Minatelli et al.

(10) Patent No.: US 9,295,699 B2
(45) Date of Patent: *Mar. 29, 2016

(54) KRILL OIL AND CAROTENOID COMPOSITION, ASSOCIATED METHOD AND DELIVERY SYSTEM

(71) Applicant: U.S. NUTRACEUTICALS, LLC, Eustis, FL (US)

(72) Inventors: John A. Minatelli, Mount Dora, FL (US); W. Stephen Hill, Ocala, FL (US); Rudi E. Moerck, Sanford, FL (US)

(73) Assignee: U.S. NUTRACEUTICALS, LLC, Eustis, FL (US)

(*) Notice: Subject to any disclaimer, the term of this patent is extended or adjusted under 35 U.S.C. 154(b) by 0 days.

This patent is subject to a terminal disclaimer.

(21) Appl. No.: 14/023,612

(22) Filed: Sep. 11, 2013

(65) Prior Publication Data

US 2014/0010868 A1 Jan. 9, 2014

Related U.S. Application Data

(60) Division of application No. 13/553,025, filed on Jul. 19, 2012, now abandoned, which is a continuation-in-part of application No. 12/840,396, filed on Jul. 21, 2010, now abandoned.

(60) Provisional application No. 61/227,881, filed on Jul. 23, 2009.

(51) Int. Cl.
| | |
|---|---|
| *A61K 31/047* | (2006.01) |
| *A61K 31/122* | (2006.01) |
| *A61K 35/612* | (2015.01) |
| *A61K 31/202* | (2006.01) |
| *A61K 31/015* | (2006.01) |
| *A61K 31/05* | (2006.01) |

(52) U.S. Cl.
CPC ............ *A61K 35/612* (2013.01); *A61K 31/015* (2013.01); *A61K 31/047* (2013.01); *A61K 31/05* (2013.01); *A61K 31/122* (2013.01); *A61K 31/202* (2013.01)

(58) Field of Classification Search
CPC .......................... A61K 31/047; A61K 31/122
See application file for complete search history.

(56) References Cited

U.S. PATENT DOCUMENTS

| 3,096,357 | A | 7/1963 | Plapper et al. |
|---|---|---|---|
| 4,829,088 | A | 5/1989 | Doulakas |
| 5,527,533 | A | 6/1996 | Tso et al. |
| 6,482,877 | B2 | 11/2002 | Inoue et al. |
| 6,716,447 | B1 | 4/2004 | Lang |
| 7,867,963 | B2 | 1/2011 | Futterer et al. |
| 8,633,255 | B2 | 1/2014 | Crews |
| 8,636,993 | B2 | 1/2014 | Scholz et al. |
| 2005/0058704 | A1 | 3/2005 | Schneider et al. |
| 2007/0141170 | A1 | 6/2007 | Lang |
| 2007/0191307 | A1 | 8/2007 | Bartlett et al. |
| 2011/0021465 | A1 | 1/2011 | Minatelli et al. |
| 2011/0237548 | A1 | 9/2011 | Minatelli et al. |
| 2011/0268811 | A1 | 11/2011 | Minatelli et al. |

FOREIGN PATENT DOCUMENTS

| EP | 1 932 521 | 6/2008 |
|---|---|---|
| JP | 2008 271878 | 11/2008 |
| KR | 10-2009-0070161 | 7/2009 |
| WO | 2006116755 | 11/2006 |
| WO | 2007/062274 | 5/2007 |
| WO | 2007/076416 | 7/2007 |
| WO | 2010/106571 | 9/2010 |

OTHER PUBLICATIONS

Moerck, "Astaxanthin & Key Carotenoids: Creating Leading Edge Eye Healthcare Formulations", Nov. 2009, retrieved from internet: http://usnutra.com/images/zanthinvitafoodsnew.pdf, pp. 1-35.

"Krill Oil Monograph", Alternative Medicine Review, Jun. 2010, retrieved from internet: http://www.thorne.com/altmedrev/.fulltest/15/1/84,pdf, pp. 84-86.

Europharma: "Vectomega", Jan. 2010, retrieved from internet: http://www.europharmausa.com/dbfiles/documents/49.pdf, pp. 1-2.

Mitchell, "Krill Oil: Better Than Fish Oil?" Jun. 28, 2009, Retrieved from the Internet: http://www.examiner.com/alternative-medicine-in-phoenix/krill-oil-better-than-fish-oil, 2 pages.

(Continued)

*Primary Examiner* — Zohreh Fay
(74) *Attorney, Agent, or Firm* — Allen, Dyer, Doppelt, Milbrath & Gilchrist, P.A.

(57) ABSTRACT

A medicine delivery system includes an inner capsule containing carotenoids and an outer capsule in which the inner capsule is contained within the outer capsule and the outer capsule containing a therapeutically effective amount of krill oil. In one example, the carotenoids comprise at least S,S'-astaxanthin derived from *Haematococcus pluvialis*, and one or more of lutein and/or trans-zeaxanthin or meso-zeaxanthin. The medicine delivery system also includes 0.5 to 8 mg of astaxanthin, 2 to 15 mg of lutein and 0.2 to 12 mg of trans-zeaxanthin contained within the inner capsule. In a specific example, the medicine delivery system includes about 4 mg of astaxanthin, about 10 mg of lutein and about 1.2 mg of trans-zeaxanthin contained within the inner capsule.

7 Claims, 7 Drawing Sheets

(56) References Cited

OTHER PUBLICATIONS

Kogan, "Krill Oil a Potential Ocular Anti-Inflammatory," Primary Care Optometry News Symposium, Jun. 1, 2006, retrieved from the Internet: http://s129638273.onlinehome.us/pharmanexmd/Files/2006-06-01-PrimaryCareOptometryNewsKrillOil.pdf, 3 pages.

"Neptune Krill Oil's Unique Properties," Internet Citation, Sep. 30, 2011, http://www.nowfoods.com/Products/ProductFAQs/081008.htm, 3 pages.

"Neptune Krill Oil's Unique Properties", Internet Citation, Sep. 30, 2011, Retrieved Sep. 30, 2011 From: URL:http://www.nowfoods.com/Products/ProductFAQs/081008/htm, pp. 1-3.

Anshel, "Examining AREDS2 Study Results," Natural Products Insider, vol. 18, No. 5, Sep./Oct. 2013, 2 pages.

Chew, "Lutein + Zeaxanthin and Omega-3 Fatty Acids for Age-Related Macular Degeneration," JAMA, May 15, 2013, vol. 309, No. 19, pp. 2005-2015.

Arnold et al., "Macular Xanthophylls and ω-3 Long-Chain Polyunsaturated Fatty Acids in Age-Related Macular Degeneration," JAMA Ophthalmology, vol. 131, No. 5, May 2013, pp. 564-572.

Chew, Lutein/Zeaxanthin for the Treatment of Age-Related Cataract AREDS2 Randomized Trial Report No. 4, JAMA Ophthalmology, Jul. 2013, vol. 131, No. 7, pp. 843-850.

"Age-Related Eye Disease Study 2 (AREDS2)," Retrieved from Internet on May 15, 2012, http://clinicaltrials.gov/ct2/show/study/NCT00345176; 4 pages.

"New Nationwide Study Will Evaluate Effect of Antioxidants and Fish Oil on Progression of Age-Related Macular Degeneration (AMD)," NEI Press Release, National Institute of Health, National Eye Institute, Oct. 12, 2006; Retrieved from the Internet May 15, 2012; http://www.nei.nih.gov/news/pressreleases/101206.asp; 3 pages.

Maoka et al., "Stereochemical Investigation of Carotenoids in the Antarctic Krill Euphausia Superba," Bulletin of the Japanese Society of Scientific Fisheries, 51(10), 1985, pp. 1671-1673.

Breithaupt, "Identification and Quantification of Astaxanthin Esters in Shrimp (Pandalus Borealis) and in a Microalga (Haematococcus Pluvialis) by Liquid Chromatography-Mass Spectrometry Using Negative Ion Atmospheric Pressure Chemical Ionization," Institut fur Lebensmittelchemic, Apr. 14, 2004; 6 pages.

Daniells, "Battle of the Omega 3 Forms; Triglycerides, Ethyl Esters or Phospholipids?" Retrieved from the Internet Nov. 10, 2013, http://www.nutraingredients-usa.com/Research/Battle-of-the-omega-3-forms-Triglycerides-ethyl-esters . . . ; 6 pages.

"Phospholipid," Wikipedia article, Retrieved from the Internet on Nov. 10, 2013, http://en.wikipedia.org/wiki/Phospholipid; 10 pages.

Romano, "Which Form of Omega 3 is Most Bioavailable?" Retrieved from the Internet on Nov. 10, 2013, http://www.vpxsports.com/article-detail/supplements/which-form-of-omega-3-is-most-bioavailable; 3 pages.

Schuchardt et al., "Incorporation of EPA and DHA into Plasma Phospholipids in Response to Different Omega-3 Fatty Acid Formulations—A Comparative Bioavailability Study of Fish Oil vs. Krill Oil," Lipids in Health and Disease, 2011, 10:145; 7 pages.

Rimfrost Krill, "Phospholipid Blog Series Part II: Increased Bioefficiency Allows Smaller Doses," Retrieved from the Internet on Nov. 10, 2013, http://www.rimfrostkrill.com/phospholipid-blog-series-part-ii-increased-bioefficiency-allows-smaller-doses; 3 pages.

Bunea et al., "Evaluation of the Effects of Neptune Krill Oil on the Clinical Course of Hyperlipidemia," Thorne Research, Inc., Alternative Medicine Review, vol. 9, No. 4, 2004; pp. 420-428.

"Krill Oil May Help Boost Lutein Absorption, Company Claims," Jan. 12, 2015, Retrieved from the Internet on Feb. 12, 2015, http://www.nutritionaloutlook.com/150112/krill, 2 pages.

THIRTEEN DAYS STABILITY DATA OF EXPERIMENTAL EHP BLENDS

DESCRIPTION OF VARIOUS FORMULATION BLENDS

| SAMPLE | ZANTHIN | | | XANMAX | | | AKER KO | | TOTAL WEIGHT (g) |
|---|---|---|---|---|---|---|---|---|---|
| | ADDED (g) | ASTA (%) | ASTA (g) | ADDED (g) | LUT (%) | ZEA (%) | LUT (g) | ZEA (g) | ADDED (g) |
| 3/1 | 1.90 | 6.07[a] | 0.12 | 0.00 | 21.15 | 2.16 | 0.00 | 0.00 | 7.00 | 8.90 |
| 4/1 | 1.49 | 6.07 | 0.09 | 0.94 | 21.15 | 2.16 | 0.20 | 0.02 | 5.51 | 7.94 |
| 5/1 | 1.90 | 6.07 | 0.12 | 1.20 | 21.15 | 2.16 | 0.25 | 0.03 | 0.00 | 3.10 |

HPLC ANALYTICAL DATA FOR DAY 1 AND DAY 13 FOR EACH FORMULATION

| | CALCULATED | | | FOUND (DAY 1) | | | FOUND (DAY 13) | | |
|---|---|---|---|---|---|---|---|---|---|
| SAMPLE | ASTA (%) | LUT (%) | ZEA (%) | ASTA (%) | LUT (%) | ZEA (%) | ASTA (%) | LUT (%) | ZEA (%) |
| 3/1 | 1.30 | 0 | 0 | 1.34 | 0 | 0 | 1.02 | 0 | 0 |
| 4/1 | 1.14 | 2.50 | 0.26 | 1.19 | 2.35 | 0.26 | 0.91 | 2.32 | 0.25 |
| 5/1 | 3.72 | 8.19 | 0.84 | 4.05 | 7.83 | 0.86 | 3.98 | 7.03 | 0.76 |

PERCENT REDUCTION OF ORIGINAL DAY 1 CAROTENOID LEVELS AS MEASURED BY HPLC

| | FROM DAY 1 TO DAY 13 | | |
|---|---|---|---|
| SAMPLE | ASTA (%) | LUT (%) | ZEA (%) |
| 3/1 | 23.9 | 0 | 0 |
| 4/1 | 23.5 | 1.3 | 3.8 |
| 5/1 | 1.7 | 10.2[b] | 11.6[b] |

FIG. 2

1. ZANTHIN USED IS: ZANTHIN 7%, LOT #100428 HAOR, → 6.07% Ax
2. SAMPLE 3/1 IS A MIXTURE OF ZANTHIN AND AKER KO 21.35 wt% ZANTHIN, → 1.29% Ax
3. SAMPLE 4/1 IS A MIXTURE OF ZANTHIN, AKER KO, AND LUTEIN, 18.82 wt% ZANTHIN, → 1.14% Ax
4. SAMPLE 5/1 IS A MIXTURE OF ZANTHIN AND LUTEIN, 61.29 wt% ZANTHIN → 3.71% Ax a. THIS ASSAY WAS OBTAINED BY RUNNING 7% ZANTHIN ON $C_{30}$ COLUMN TOGETHER WITH DAY 1 SAMPLES. THEREFORE IT (BUT NOT THE CofA ASSAY) WAS USED FOR FURTHER CALCULATIONS.
b. ENORMOUSLY HIGH REDUCTION OF LUTEIN AND ZEAXANTHIN CONCENTRATIONS MAY BE DUE TO BAD BLEND UNIFORMITY. XANMAX SEDIMENT IS RATHER DIFFICULT TO EVENLY DISTRIBUTE IN THE ENTIRE VOLUME.

STABILITY ANALYTICAL REPORT

| SAMPLE: LAB ID/LOT/NAME | ASTAXANTHIN (%) | | | LUTEIN (%) | | | ZEAXANTHIN (%) | | |
|---|---|---|---|---|---|---|---|---|---|
| | DAY 0 | DAY 12 | % CHANGE | DAY 0 | DAY 12 | % CHANGE | DAY 0 | DAY 12 | % CHANGE |
| U2031-5/110113A/EYEPRO A | 0.78 | 0.56 | 28.2 | 2.63 | 2.52 | 4.2 | 0.29 | 0.27 | 6.9 |
| U2031-6/110113E/EYEPRO E | 0.80 | 0.67 | 16.3 | 2.53 | 2.16 | 14.6 | 0.28 | 0.23 | 17.9 |
| U2031-7/110114A/FLEXPRO A | 0.54 | 0.40 | 25.9 | | | | | | |
| U2031-8/110114E/FLEXPRO E | 0.57 | 0.55 | 3.5* | | | | | | |

DAY 12, 20° C

*FIG. 3*

* INCONSISTENCY OF RESULTS MAY BE DUE TO INCONSISTENT VISCOSITY OF THE SAMPLE U2031-8

STABILITY ANALYTICAL REPORT

| SAMPLE: LAB ID/LOT/NAME | ASTAXANTHIN (%) | | | LUTEIN (%) | | | ZEAXANTHIN (%) | | |
|---|---|---|---|---|---|---|---|---|---|
| | DAY 0 | DAY 12 | % CHANGE | DAY 0 | DAY 12 | % CHANGE | DAY 0 | DAY 12 | % CHANGE |
| U2031-1/110113A/EYEPRO A | 0.78 | 0.12 | 84.6 | 2.63 | 2.44 | 7.2 | 0.29 | 0.28 | 3.4 |
| U2031-2/110113E/EYEPRO E | 0.80 | 0.50 | 37.5 | 2.53 | 2.24 | 11.5 | 0.28 | 0.24 | 14.3 |
| U2031-3/110114A/FLEXPRO A | 0.54 | 0.10 | 81.5 | | | | | | |
| U2031-4/110114E/FLEXPRO E | 0.57 | 0.36 | 36.8 | | | | | | |

DAY 12, 50° C

FIG. 4

ADDENDUM

SUMMARY OF CHANGES BY UV (AS ASTAXANTHIN)

| SAMPLE | DAY 0 | 20°C | | 50°C | |
|---|---|---|---|---|---|
| | | DAY 12 | % CHANGE | DAY 12 | % CHANGE |
| EYEPRO (AKER) | 5.09 | 4.95 | 2.8 | 4.63 | 9.0 |
| EYEPRO (ENZYMOTEC) | 4.75 | 4.40 | 7.4 | 4.33 | 8.8 |
| FLEXPRO (AKER) | 0.93 | 0.91 | 2.2 | 0.81 | 12.9 |
| FLEXPRO (ENZYMOTEC) | 0.99 | 0.98 | 1.0 | 0.86 | 13.1 |

FIG. 5

ASTAXANTHIN STABILITY ANALYTICAL REPORT
DAY 26

20°C

| SAMPLE: LAB ID/LOT/NAME | %ASSAY | | | CHANGES (% OF ASSAY REDUCTION) | | |
|---|---|---|---|---|---|---|
| | DAY 0 | DAY 12 | DAY 26 | DAYS 0-12 | DAYS 12-26 | DAYS 0-26 |
| U2044-5/110113A/EYEPRO A | 0.78 | 0.56 | 0.43 | 28.2 | 23.2 | 44.9 |
| U2044-6/110113E/EYEPRO E | 0.80 | 0.67 | 0.68 | 16.3 | -1.5 | 15.0 |
| A=AKER KRILL OIL | | | | | | |
| E=ENZYMOTEC KRILL OIL | | | | | | |

50°C

| SAMPLE: LAB ID/LOT/NAME | %ASSAY | | | CHANGES (% OF ASSAY REDUCTION) | | |
|---|---|---|---|---|---|---|
| | DAY 0 | DAY 12 | DAY 26 | DAYS 0-12 | DAYS 12-26 | DAYS 0-26 |
| U2044-5/110113A/EYEPRO A | 0.78 | 0.12 | 0.10 | 84.6 | 16.7 | 87.2 |
| U2044-6/110113E/EYEPRO E | 0.80 | 0.50 | 0.30 | 37.5 | 40.0 | 62.5 |
| A=AKER KRILL OIL | | | | | | |
| E=ENZYMOTEC KRILL OIL | | | | | | |

* QUANTIFICATION OF LUTEIN AND ZEAXANTHIN IS NOT DONE AT THIS POINT BECAUSE OF FORMATION OF A DENSE XANMAX CAKE ON THE BOTTOM OF STORAGE CONTAINERS AND PREDICTABLE INCONSISTENCY OF THE CORRESPONDING RESULTS THEREFORE.

FIG. 6

KRILL OIL AND CAROTENOID COMPOSITION, ASSOCIATED METHOD AND DELIVERY SYSTEM

RELATED APPLICATION(S)

This application is a divisional of Ser. No. 13/553,025 filed Jul. 19, 2012, which is a continuation-in-part of U.S. patent application Ser. No. 12/840,396 filed Jul. 21, 2010, which is based on provisional patent application Ser. No. 61/227,881, filed Jul. 23, 2009.

FIELD OF THE INVENTION

The present invention relates to a krill oil and carotenoid composition used for eye care or other medical applications and medicine delivery system for the composition. The present invention also relates to a method of preventing, retarding and ameliorating central nervous system and eye diseases, including treating eye insult resulting from disease or injury, such as age-related macular degeneration, photic injury, photoreceptor cell or ganglion cell damage, ischemic insult-related diseases, cataracts, dry eye syndromes and inflammatory diseases.

BACKGROUND OF THE INVENTION

The eye is an extension of the brain, and therefore a part of the central nervous system. Accordingly, in the case of an eye injury or disease, i.e., a retinal injury or disease, the diseases are often without treatment and the eye cannot be transplanted. Eye diseases and injuries that presently are untreatable include retinal photic injury, retinal ischemia-induced eye injury, age-related macular degeneration, and other eye diseases and injuries that are induced by singlet oxygen and other free radical species.

It has been hypothesized that a major cause of these untreatable retinal and other eye diseases and injuries is the generation and presence of singlet oxygen and other free radical species. Singlet oxygen and free radical species can be generated by a combination of light, oxygen, other reactive oxygen species like hydrogen peroxide, superoxide or during reperfusion after an ischemic insult resulting in highly reactive NOx release.

The eye is subjected to continuous light exposure because the primary purpose of the eye is light perception. Therefore, some untreatable diseases and injuries to the eye result from the continuous exposure of the eye to light, coupled with the highly-oxygenated environment in the eye.

The process of light perception is initiated in the photoreceptor cells. The photoreceptor cells are a constituent of the outer neuronal layer of the retina, which is a component of the central nervous system. The photoreceptor cells are well sheltered in the center of the eye, and are protected structurally by the sclera, nourished by the highly-vascularized uvea and safeguarded by the blood-retinal barrier of the retinal pigmented epithelium.

The primary function of the photoreceptor cells is to convert light into a physic-chemical signal (transduction) and to transmit this signal to the other neurons (transmission). During the transduction and transmission processes, the metabolic activities of these neurons are changed dramatically. Even though the photoreceptor cells are securely protected in the interior of the eye, these cells are readily accessible to light because their primary function is light detection. Excessive light energy reaching the retina can cause damage to these neurons, either directly or indirectly, by overwhelming the metabolic systems of these cells.

The combination of continuous and/or excessive exposure to light, and the relatively high concentration of oxygen in the eye, generates singlet oxygen and other free radical species. Singlet oxygen and free radical species also can be generated by enzymatic processes independent from light exposure. The free radical species and singlet oxygen are reactive entities that can oxidize polyunsaturated fatty acids. The retina contains the highest concentration of polyunsaturated fatty acids of any tissue in the human body, and per-oxidation of the polyunsaturated fatty acids in cell membranes of the retina by hydroxyl radicals (OH) or superoxide ($O_2$) radicals can propagate additional free radical species. These free radical species can lead to functional impairment of the cell membranes and cause temporary or permanent damage to retinal tissue. It has been theorized that the generation of singlet oxygen and free radical species therefore underlies the pathogenesis of light-induced retinopathy and post-ischemic reflow injury. In addition, a deficiency in removing these reactive free radical species can also contribute to various diseases of the eye.

A number of natural mechanisms protect the photoreceptor cells from light injury. For example, the ocular media, including the cornea, aqueous, lens, and vitreous, filter most of the light in the ultraviolet region. However, after cataract extraction or other surgical intervention, some of these protective barriers are removed or disturbed, whereby the photoreceptor cells are more susceptible to damage by radiant energy. The photoreceptor cells also possess other forms of protection from photic injury, for example, the presence of antioxidant compounds to counteract the free radical species generated by light. As will be demonstrated hereafter, antioxidants, which quench and/or scavenge singlet oxygen, hydrogen peroxide, superoxide and radical species, minimize injury to the photoreceptor cells. The most-important area of the retina where such protection is necessary is the fovea or central region of the macula. Even though several protective mechanisms are present in the eye, a leading cause of blindness in the United States is age-related photoreceptor degeneration. Clinically, photoreceptor degeneration, as seen in age-related macular degeneration, is causally related to excessive exposure to high energy UVA and UVB ultraviolet light. The causes of age-related macular degeneration, which is characterized by a loss of photoreceptor neurons resulting in decreased vision, are still being investigated. Epidemiological studies indicate that age-related photoreceptor degeneration, or age-related macular degeneration, is related to several factors including age, sex, family history, color of the iris, nutritional deficiency, immunologic disorders, cardiovascular and respiratory diseases and pre-existing eye diseases. Advancing age is the most significant factor. Recently, it has been demonstrated that aging eyes have a decreased amount of carotenoids deposited on the retina. Clinical and laboratory studies indicate that photic injury is at least one cause of age-related macular degeneration because of the cumulative effect of repeated mild photic insult which leads to a gradual loss of photoreceptor cells.

Age-related macular degeneration is an irreversible blinding disease of the retina. Unlike cataracts which can be restored by replacing the diseased lens, age-related macular degeneration cannot be treated by replacing the diseased retina because the retina is a component of the central nervous system. Therefore, because no treatment for this disease exists once the photoreceptors are destroyed, prevention is the only way to address age-related macular degeneration. Presently, prevention of age-related macular degeneration resides in limiting or preventing light and oxygen-induced (i.e., free radical-induced) damage to the retina because the retina is the only organ that is continuously exposed to high levels of light in a highly-oxygenated environment.

In addition to photic injury, eye injury and disease can result from singlet oxygen and free radical species generated during reperfusion after an ischemic insult. Ischemic insult to retinal ganglion cells and to neurons of the inner layers of retina causes loss of vision. Loss of vision accompanies diabetic retinopathy, retinal arterial occlusion, retinal venous occlusion and glaucoma, each of which insults the eye depriving the eye of oxygen and nutrition via ischemic insult.

The damage to the retinal ganglion cells has been attributed to ischemia, and subsequent reperfusion during which free radicals are generated.

The pathogenesis of photic injury, of age-related macular degeneration, of ischemia/reperfusion damage, of traumatic injury and of inflammations of the eye have been attributed to singlet oxygen and free radical generation, and subsequent free radical-initiated reactions. Investigators therefore studied the role of antioxidants in preventing or ameliorating these diseases and injuries of the central nervous system in general, and the eye in particular.

For example, ascorbate was investigated as an agent to treat retinal photic injury. Ascorbate is a reducing agent which is present in the retina in a high concentration. Studies indicated that ascorbate in the retina can act as an antioxidant and is oxidized by free radical species generated during excessive light exposure.

Administration of ascorbate reduced the loss of rhodopsin after photic exposure, thereby suggesting that ascorbate offered protection against retinal photic injury. A decrease in rhodopsin levels is an indicator of photic eye injury. The protective effect of ascorbate is dose-dependent, and ascorbate was effective when administered before light exposure. Morphometric studies of the photoreceptor nuclei remaining in the retina after light exposure showed that rats given ascorbate supplements had substantially less retinal damage. Morphologically, rats with ascorbate supplements also showed better preservation of retinal pigmented epithelium.

The above studies led to the hypothesis that ascorbate mitigates retinal photic injury because of its antioxidant properties, which are attributed to its redox properties. Ascorbate is a scavenger of superoxide radicals and hydroxy radicals and also quenches singlet oxygen, all of which are formed during retinal photic injury. This hypothesis accounts for the presence of high levels of naturally-occurring ascorbate in a normal retina.

Therefore, antioxidants which inhibit free radical formation, or which quench singlet oxygen and scavenge free radical species, can decrease lipid per-oxidation and ameliorate photic injury and ischemic/reperfusion injury in the retina. Antioxidants originally were investigated because they are known constituents of human tissue. However, antioxidants that are not naturally occurring in human tissue were also tested. In particular, in addition to ascorbate, antioxidants such as 2,6-di-tert-butylphenol, gamma-oryzanol, alpha-tocopherol, mannitol, reduced glutathione, and various carotenoids, including lutein, zeaxanthin and astaxanthin have been studied for an ability to comparatively quench singlet oxygen and scavenge free radical species in vitro. These and other antioxidants have been shown in vitro to be effective quenchers and scavengers for singlet oxygen and free radicals. In particular, the carotenoids, as a class of compounds, are very effective singlet oxygen quenchers and free radical scavengers. However, individual carotenoids differ in their ability to quench singlet oxygen and scavenge for free radical species.

The carotenoids are naturally-occurring compounds that have antioxidant properties. The carotenoids are common compounds manufactured by plants, and contribute greatly to the coloring of plants and some animals. A number of animals, including mammals, are unable to synthesize carotenoids de novo and accordingly rely upon diet to provide carotenoid requirements. Mammals also have a limited ability to modify carotenoids. A mammal can convert beta-carotene to vitamin A, but most other carotenoids are deposited in mammalian tissue in unchanged form.

With respect to humans, about ten carotenoids are found in human serum. The major carotenoids in human serum are beta-carotene, alpha-carotene, cryptoxanthin, lycopene and lutein. Small amounts of zeaxanthin, phytofluene, and phytoene are found in human organs. However, of the ten carotenoids found in human serum, only two, trans- and/or meso-zeaxanthin and lutein, have been found in the human retina. Zeaxanthin is the predominant carotenoid in the central macula or foveal region and is concentrated in the cone cells in the center of the retina, i.e., the fovea. Lutein is predominantly located in the peripheral retina in the rod cells. Therefore, the eye preferentially assimilates zeaxanthin over lutein in the central macula which is a more effective singlet oxygen scavenger than lutein. It has been theorized that zeaxanthin and lutein are concentrated in the retina because of their ability to quench singlet oxygen and scavenge free radicals, and thereby limit or prevent photic damage to the retina.

Therefore only two of the about ten carotenoids present in human serum are found in the retina. Beta-carotene and lycopene, the two most abundant carotenoids in human serum, either have not been detected or have been detected only in minor amounts in the retina. Beta-carotene is relatively inaccessible to the retina because beta-carotene is unable to cross the blood-retinal brain barrier of the retinal pigmented epithelium effectively. It also is known that another carotenoid, canthaxanthin, can cross the blood-retinal brain barrier and reach the retina. Canthaxanthin, like all carotenoids, is a pigment and can discolor the skin. Canthaxanthin provides a skin color that approximates a suntan, and accordingly has been used by humans to generate an artificial suntan. However, an undesirable side effect in individuals that ingested canthaxanthin at high doses for an extended time was the formation of crystalline canthaxanthin deposits in the inner layers of the retina. Therefore, the blood-retinal brain barrier of the retinal pigmented epithelium permits only particular carotenoids to enter the retina. The carotenoids other than zeaxanthin and lutein that do enter the retina cause adverse effects, such as the formation of crystalline deposits by canthaxanthin, which may take several years to dissolve. Canthaxanthin in the retina also caused a decreased adaptation to the dark.

Investigators have unsuccessfully sought additional antioxidants to further counteract the adverse affects of singlet oxygen and free radical species on in the eye. The investigators have studied the antioxidant capabilities of several compounds, including various carotenoids. Even though the carotenoids are strong antioxidants, investigators have failed to find particular carotenoids among the 600 naturally-occurring carotenoids that effectively quench singlet oxygen and scavenge for free radical species, that are capable of crossing the blood-retinal brain barrier, that do not exhibit the adverse affects of canthaxanthin after crossing the blood-retinal brain barrier, and that ameliorate eye disease or injury and/or retard the progression of a degenerative disease of the eye and are more potent anti-oxidants than either lutein or zeaxanthin.

Many scientific papers are directed to eye diseases and injuries, such as age-related macular degeneration, causes of the damage resulting from the diseases or injuries, and attempts to prevent or treat such diseases and injuries. The publications, which discuss various antioxidants, including the carotenoids and other antioxidants like alpha-tocopherol, include:

M. O. M. Tso, "Experiments on Visual Cells by Nature and Man: In Search of Treatment for Photoreceptor Degeneration," Investigative Ophthalmology and Visual Science, 30(12), pp. 2421-2454 (December, 1989);

W. Schalch, "Carotenoids in the Retina—A Review of Their Possible Role in Preventing or Limiting Damage Caused by Light and Oxygen," Free Radicals and Aging, I. Emerit et al. (ed.), Birkhauser Verlag, pp. 280-298 (1992);

M. O. M. Tso, "Pathogenetic Factors of Aging Macular Degeneration," Ophthalmology, 92(5), pp. 628-635 (1985);

M. Mathews-Roth, "Recent Progress in the Medical Applications of Carotenoids," Pure and Appl. Chem., 63(1), pp. 147-156 (1991);

W. Miki, "Biological Functions and Activities of Animal Carotenoids," Pure and Appl. Chem., 63(1), pp. 141-146 (1991);

M. Mathews-Roth, "Carotenoids and Cancer Prevention-Experimental and Epidemiological Studies," Pure and Appl. Chem., 57(5), pp. 717-722 (1985);

M. Mathews-Roth, "Porphyrin Photosensitization and Carotenoid Protection in Mice; In Vitro and In Vivo Studies," Photochemistry and Photobiology, 40(1), pp. 63-67 (1984);

P. DiMascio et al., "Carotenoids, Tocopherols and Thiols as Biological Singlet Molecular Oxygen Quenchers," Biochemical Society Transactions, 18, pp. 1054-1056 (1990);

T. Hiramitsu et al., "Preventative Effect of Antioxidants on Lipid Peroxidation in the Retina," Ophthalmic Res., 23, pp. 196-203 (1991);

D. Yu et al., "Amelioration of Retinal Photic Injury by Beta-Carotene," ARVO Abstracts Invest. Ophthalmol. Vis. Sci., 28 (Suppl.), p. 7, (1987);

M. Kurashige et al., "Inhibition of Oxidative Injury of Biological Membranes by Astaxanthin," Physiol. Chem. Phys. and Med. NMR, 22, pp. 27-38 (1990); and N. I. Krinsky et al., "Interaction of Oxygen and Oxyradicals With Carotenoids," J. Natl. Cancer Inst., 69(1), pp. 205-210 (1982).

Anon., "Bio & High Technology Announcement Itaro," Itaro Refrigerated Food Co., Ltd.

Anon., "Natural Astaxanthin & Krill Lecithin," Itaro Refrigerated Food Co., Ltd.

Johnson, E. A. et al., "Simple Method for the Isolation of Astaxanthin from the Basidomycetous Yeast Phaffia rhodozyma," App. Environ. Microbiol., 35(6), pp. 1155-1159 (1978).

Kirschfeld, K., "Carotenoid Pigments: Their Possible Role in Protecting Against Photooxidation in Eyes and Photoreceptor Cells," Proc. R. Soc. Land., B216, pp. 71-85 (1982).

Latscha, T., "Carotenoids-Carotenoids in Animal Nutrition," Hoffmann-LaRoche Ltd., Basel, Switzerland.

Li, Z. et al., "Desferrioxime Ameliorated Retinal Photic Injury in Albino Rats," Current Eye Res., 10(2), pp. 133-144 (1991).

Mathews-Roth, M., "Porphyrin Photosensitization and Carotenoid Protection in Mice; In Vitro and In Vivo Studies," Photochemistry and Photobiology, 40(1), pp. 63-67 (1984).

Michon, J. J. et al., "A Comparative Study of Methods of Photoreceptor Morphometry," Invest. Ophthalmol. Vis. Sci., 32, pp. 280-284 (1991).

Tso, M. O. M., "Pathogenetic Factors of Aging Mascular Degeneration," Ophthalmology, 92(5), pp. 628-635 (1985).

Yu, D. et al., "Amelioration of Retinal Photic Injury by Beta-Carotene," ARVO Abstracts Invest. Ophthalmol. Vis. Sci., 28 (Suppl.), p. 7, (1987).

In general, the above-identified publications support the hypothesis that singlet oxygen and free radical species are significant contributors to central nervous system, and particularly eye injury and disease. For example, it has reported that consumption of an antioxidant, such as ascorbic acid (Vitamin C), alpha-tocopherol (Vitamin E) or beta-carotene (which is converted in vivo to lutein), can decrease the prevalence of age-related macular degeneration.

The above-identified publications also demonstrated that several carotenoids, including astaxanthin, are strong antioxidants compared to beta-carotene, ascorbic acid and other widely used antioxidants in vitro. The publications also relate that (1) only particular carotenoids selectively cross the blood-retinal brain barrier, and that (2) certain carotenoids other than zeaxanthin and lutein that cross the blood-retinal brain barrier cause adverse affects.

In general, the above-identified publications teach that astaxanthin is a more effective antioxidant than carotenoids such as zeaxanthin, lutein, tunaxanthin, canthaxanthin, beta-carotene, and alpha-tocopherol in vitro. For example, the in vitro and in vivo studies disclosed in the Kurashige et al. publication with respect to astaxanthin demonstrated that the mean effective concentration of astaxanthin which inhibits lipid peroxidation was 500 times lower than that of alpha-tocopherol. Similarly, the Miki publication discloses that, in vitro, astaxanthin exhibits a strong quenching effect against singlet oxygen and a strong scavenging effect against free radical species.

This free radical theory of retinal damage has been advanced by investigators examining the effectiveness of various antioxidants in ameliorating these diseases.

To date, investigative efforts have been directed to preventing diseases and injury because the resulting free radical-induced damage is not effectively treatable. Therefore, a need exists for a method not only to prevent or retard, but also to ameliorate, degenerative and traumatic diseases and injuries to the central nervous system, and particularly the eye. The copending '396 parent application discloses a therapeutically effective amount of a synergistic multi-ingredient composition of mixed carotenoids comprising at least S,S'-astaxanthin derived from *Haematococcus pluvialis*, and one or more of lutein and/or trans-zeaxanthin or meso-zeaxanthin admixed with a therapeutically effective amount of krill oil containing phospholipid bound and triglyceride bound EPA and DHA in which said krill oil contains at least 30% total phospholipids. The composition includes 50 to 1000 mg of krill oil, 0.5 to 8 mg of astaxanthin, 2 to 15 mg of lutein and 0.2 to 12 mg of trans-zeaxanthin.

Unexpectedly, it has been found that the addition of carotenoids and especially astaxanthin to krill oil results in an apparent chemical reaction between the two components with the possible trans-esterification occurring between the krill oil fatty acid esters and partially esterified carotenoids and creating a new compound. Therefore, a delivery mechanism is beneficial for the composition to prevent the disappearance of carotenoids. The "reacted" carotenoids could also be beneficial in an associated method of treating and composition.

SUMMARY OF THE INVENTION

A medicine delivery system includes an inner capsule containing carotenoids and an outer capsule in which the inner capsule is contained within the outer capsule and the outer capsule containing a therapeutically effective amount of krill oil. In one example, the carotenoids comprise at least S,S'-astaxanthin derived from *Haematococcus pluvialis*, and one or more of lutein and/or trans-zeaxanthin or meso-zeaxanthin. The medicine delivery system also includes 0.5 to 8 mg of astaxanthin, 2 to 15 mg of lutein and 0.2 to 12 mg of trans-zeaxanthin contained within the inner capsule. In a specific example, the medicine delivery system includes about 4 mg of astaxanthin, about 10 mg of lutein and about 1.2 mg of trans-zeaxanthin contained within the inner capsule.

In another example, the krill oil contains phospholipid bound and triglyceride bound EPA and DHA and the krill oil contains at least 30% total phospholipids. In another example, the krill oil is about 50 to about 1,000 mg contained in the outer capsule.

A method of treating an individual is also set forth by administering a therapeutically effective amount of synergistic multi-ingredient composition of krill oil and carotenoids and reacting to carotenoids in vivo with the krill oil. In an example, the method includes administering carotenoids comprising at least S,S'-astaxanthin derived from *Haematococcus pluvialis* and one or more of lutein and/or trans-zeaxanthin or meso-zeaxanthin. In another example, the method includes administering 0.5 to 8 mg of astaxanthin, 2 to 15 mg of lutein and 0.2 to 12 mg of trans-zeaxanthin. About 4 mg of astaxanthin, about 10 mg of lutein and about 1.2 mg of trans-zeaxanthin can be administered. The krill oil in yet another example contains phospholipid bound and triglyceride bound EPA and DHA and about 30% total phospholipids. About 50 to 1,000 mg of krill oil can be administered.

A composition is disclosed that includes a synergistic multi-ingredient composition of krill oil containing phospholipid bound and triglyceride bound EPA and DHA in which the krill oil contains at least 30% total phospholipids and mixed carotenoids comprising at least S,S'-astaxanthin derived from *Haematococcus pluvialis* that are reacted with the krill oil, and one or more of lutein and/or trans-zeaxanthin or meso-zeaxanthin.

BRIEF DESCRIPTION OF THE DRAWINGS

Other objects, features and advantages of the present invention will become apparent from the detailed description of the invention which follows, when considered in light of the accompanying drawings in which:

FIG. 2 is chart showing stability data of various formulation blends of the composition of carotenoids and krill oil in accordance with a non-limiting example.

FIGS. 3 and 4 show stability analytical charts for various formulation blends of the composition of carotenoids and krill oil at respective 20 degrees C. and 50 degrees C. in accordance with a non-limiting example.

FIG. 5 is a chart showing a summary of changes by ultraviolet radiation of the astaxanthin in the composition in accordance with a non-limiting example.

FIG. 6 is another chart showing astaxanthin stability for the composition at 20 degrees C. and 50 degrees C.

DETAILED DESCRIPTION OF THE PREFERRED EMBODIMENTS

Figure 1:
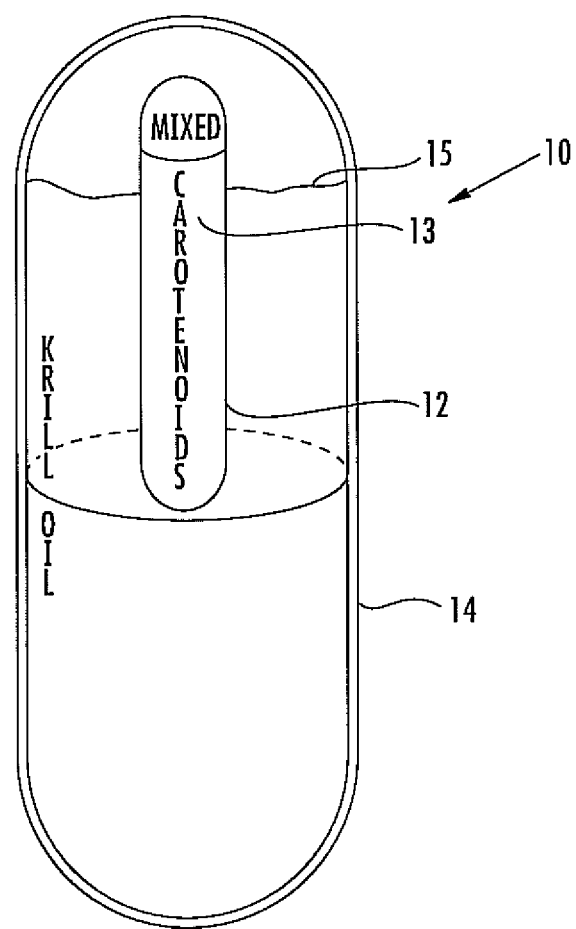
FIG. 1 is an example of a medicine delivery system that includes an inner capsule containing carotenoids and an outer capsule containing krill oil in accordance with a non-limiting example.

The present invention will now be described more fully hereinafter. This invention may, however, be embodied in many different forms and should not be construed as limited to the embodiments set forth herein. Rather, these embodiments are provided so that this disclosure will be thorough and complete, and will fully convey the scope of the invention to those skilled in the art.

The leading cause of visual loss among elderly persons is dry or atropic AMD, which has an increasingly important social and economic impact in the United States. As the size of the elderly population increases in this country, AMD will become a more prevalent cause of blindness than both diabetic retinopathy and glaucoma combined. Although laser treatment has been shown to reduce the risk of extensive macular scarring from the "wet" or neovascular form of the disease, there are currently no effective treatments for the vast majority of patients with wet AMD.

The Eye Diseases Prevalence Research Group (EDPRG) attributes AMD as the major cause of blindness among elderly people of European ancestry. Among white persons, AMD is believed to account for more than 50% of all blinding conditions.

The EDPRG estimates that approximately 1.2 million residents of the US are living with neovascular AMD and 970,000 are living with geographic atrophy, while 3.6 million are living with bilateral large drusen. In the next 20 years these values are expected to increase by 50% with projected demographic shifts.

Age-related developmental changes in retinal morphology and energy metabolism, as well as cumulative effects of environmental exposures may render the neural and vascular retina and retinal pigment epithelium more susceptible to damage in late adulthood. Along with these metabolic and structural changes and exposures, the aging eye also experiences a reduction in the potency of endogenous and exogenous defense systems. Pharmacological and surgical treatment options are of limited scope and efficacy currently. They are costly and may result in complications as severe as end-stage disease. The likelihood of vision loss among persons with neovascular AMD can be reduced with anti-VEGF treatment, photodynamic therapy, and laser photocoagulation.

Nutrient-based preventative treatments for AMD development and progression have been examined in several studies including AREDSI, a NEI-sponsored study, the LAST, TOZAL and CARMIS studies for example. AREDS was a multi-center study of the natural history of AMD and cataract. AREDS included a controlled randomized clinical trial designed to evaluate the effect of pharmacological doses of zinc and/or a formulation containing nutrients with antioxidant properties (vitamin C, vitamin E, and β-carotene) on the rate of progression to advanced AMD and on visual acuity outcomes. The use of the combination of antioxidants and zinc reduced the risk of development of advanced AMD in participants who had at least a moderate risk of developing AMD by about 25%. The overall risk of moderate vision loss [≥15 letters on the Early Treatment Diabetic Retinopathy Study (ETDRS) chart] was reduced by 19% at 5 years.

Of approximately 600 carotenoids identified in nature in the human diet, and 20 in human serum, only two forms of dietary xanthophylls, lutein and zeaxanthin, are present in human macular pigment. Lutein represents approximately 36% of all retinal carotenoids; zeaxanthin and meso-zeaxanthin each represent about 18%.

The natural tissue distribution, biochemical, and biophysical characteristics of lutein provide a reasonable basis for speculating that this nutrient acts in biological systems as: (1) an important structural molecule within cell membranes; (2) a short-wavelength light filter; (3) a modulator of intra- and extracellular reduction-oxidation (redox) balance; and (4) a modulator in signal transduction pathways. Lutein and zeaxanthin were considered for inclusion in the AREDS formulation; however, at the time of AREDS' initiation, neither carotenoid was readily available for manufacturing in a research formulation.

The evidence base suggests that macular xanthophylls in combination with omega-3 LCPUFAs from fish oil may act as modifiable factors capable of modulating processes implicated in existing AMD pathogenesis and progression and is the basis for the on-going US Government sponsored AREDS II study. Intake of these compounds may also show merit as a well-tolerated preventive intervention. Biochemical and biophysical properties of these compounds demonstrate a capacity to modulate factors and processes that activate and are activated by exposures associated with aging. These exposures include developmental changes associated with aging, chronic light exposure, alterations in energy metabolism, and cellular signaling pathways.

Dry Eye Syndrome

According to C Stephen Foster, MD, FACS, FACR, FAAO, Clinical Professor of Ophthalmology, Harvard Medical School; Consulting Staff, Department of Ophthalmology, Massachusetts Eye and Ear Infirmary; Founder and President, Ocular Immunology and Uveitis Foundation, Massachusetts Eye Research and Surgery Institution et al' dry eye is a very common disorder affecting a significant percentage (approximately 10-30%) of the population, especially those older than 40 years.

In the United States, an estimated 3.23 million women and 1.68 million men, a total of 4.91 million people, aged 50 years and older are affected.

Dry eye is a multi-factorial disease of the tears and the ocular surface that results in symptoms of discomfort, visual disturbance, and tear film instability with potential damage to the ocular surface. Dry eye is accompanied by increased osmolarity of the tear film and inflammation of the ocular surface.

The tear layer covers the normal ocular surface. Generally, it is accepted that the tear film is made up of 3 intertwined layers, as follows:

1) A superficial thin lipid layer (0.11 μm) is produced by the meibomian glands, and its principal function is to retard tear evaporation and to assist in uniform tear spreading.

2) A middle thick aqueous layer (7 μm) is produced by the main lacrimal glands (reflex tearing), as well as the accessory lacrimal glands of Krause and Wolfring (basic tearing).

3) An innermost hydrophilic mucin layer (0.02-0.05 μm) is produced by both the conjunctiva goblet cells and the ocular surface epithelium and associates itself with the ocular surface via its loose attachments to the glycocalyx of the microplicae of the epithelium. It is the hydrophilic quality of the mucin that allows the aqueous to spread over the corneal epithelium.

The lipid layer produced by the meibomian glands acts as a surfactant, as well as an aqueous barrier (retarding evaporation of the underlying aqueous layer), and provides a smooth optical surface. It may also act as a barrier against foreign particles and may also have some antimicrobial properties. The glands are holocrine in nature, and so the secretions contain both polar lipids (aqueous-lipid interface) and nonpolar lipids (air-tear interface) as well as proteinaceous material. All of these are held together by ionic bonds, hydrogen bonds, and van der Waals forces. The secretions are subject to neuronal (parasympathetic, sympathetic, and sensory sources), hormonal (androgen and estrogen receptors), and vascular regulation. Evaporative loss is predominantly due to meibomian gland dysfunction (MGD).

The aqueous component is produced by the lacrimal glands. This component includes about 60 different proteins, electrolytes, and water. Lysozyme is the most abundant (20-40% of total protein) and also the most alkaline protein present in tears. It is a glycolytic enzyme that is capable of breaking down bacterial cell walls. Lactoferrin has antibacterial and antioxidant functions, and the epidermal growth factor (EGF) plays a role in maintaining the normal ocular surface and in promoting corneal wound healing. Albumin, transferrin, immunoglobulin A (IgA), immunoglobulin M (IgM), and immunoglobulin G (IgG) are also present.

Aqueous tear deficiency (ATD) is the most common cause of dry eye, and it is due to insufficient tear production. The secretion of the lacrimal gland is controlled by a neural reflex arc, with afferent nerves (trigeminal sensory fibers) in the cornea and the conjunctiva passing to the pons (superior salivary nucleus), from which efferent fibers pass, in the nervus intermedius, to the pterygopalatine ganglion and postganglionic sympathetic and parasympathetic nerves terminating in the lacrimal glands.

Keratoconjunctivitis sicca (KCS) is the name given to this ocular surface disorder. KCS is subdivided into Sjogren syndrome (SS) associated KCS and non-SS associated KCS. Patients with aqueous tear deficiency have SS if they have associated xerostomia and/or connective tissue disease. Patients with primary SS have evidence of a systemic autoimmune disease as manifested by the presence of serum autoantibodies and very severe aqueous tear deficiency and ocular surface disease. These patients, mostly women, do not have a separate, identifiable connective tissue disease. Subsets of patients with primary SS lack evidence of systemic immune dysfunction, but they have similar clinical ocular presentation. Secondary SS is defined as KCS associated with a diagnosable connective tissue disease, most commonly rheumatoid arthritis but also SLE and systemic sclerosis.

Non-SS KCS is mostly found in postmenopausal women, in women who are pregnant, in women who are taking oral contraceptives, or in women who are on hormone replacement therapy (especially estrogen only pills). The common denominator here is a decrease in androgens, either from reduced ovarian function in the postmenopausal female or from increased levels of the sex hormone binding globulin in pregnancy and birth control pill use. Androgens are believed to be trophic for the lacrimal and meibomian glands. They also exert potent anti-inflammatory activity through the production of transforming growth factor beta (TGF-beta), suppressing lymphocytic infiltration.

Lipocalins (previously known as tear-specific prealbumin), which are present in the mucous layer, are inducible lipid-binding proteins produced by the lacrimal glands that lower the surface tension of normal tears. This provides stability to the tear film and also explains the increase in surface tension that is seen in dry eye syndromes characterized by lacrimal gland deficiency. Lipocalin deficiency can lead to the precipitation in the tear film, forming the characteristic mucous strands seen in patients with dry eye symptomatology.

The glycocalyx of the corneal epithelium contains the transmembrane mucins (glycosylated glycoproteins present in the glycocalyx) MUC1, MUC4, and MUC16. These membrane mucins interact with soluble, secreted, gel-forming mucins produced by the goblet cells (MUC5AC) and also with others like MUC2. The lacrimal gland also secretes MUC7 into the tear film.

These soluble mucins move about freely in the tear film (a process facilitated by blinking and electrostatic repulsion from the negatively charged transmembrane mucins), functioning as clean-up proteins (picking up dirt, debris, and pathogens), holding fluids because of their hydrophilic nature, and harboring defense molecules produced by the lacrimal gland. Transmembrane mucins prevent pathogen adherence (and entrance) and provide a smooth lubricating surface, allowing lid epithelia to glide over corneal epithelia with minimal friction during blinking and other eye movements. Recently, it has been suggested that the mucins are mixed throughout the aqueous layer of tears (owing to their hydrophilic nature) and, being soluble, move freely within this layer.

Mucin deficiency (caused by damage to the goblet cells or the epithelial glycocalyx), as seen in Stevens-Johnson syndrome or after a chemical burn, leads to poor wetting of the corneal surface with subsequent desiccation and epithelial damage, even in the presence of adequate aqueous tear production.

Pathophysiology

A genetic predisposition in SS associated KOS exists as evident by the high prevalence of human leukocyte antigen B8 (HLA-B8) haplotype in these patients. This condition leads to a chronic inflammatory state, with the production of auto-antibodies, including antinuclear antibody (ANA), rheumatoid factor, fodrin (a cytoskeletal protein), the muscarinic M3 receptor, or SS-specific antibodies (eg, anti-RO [SS-A], anti-LA [SS-B]), inflammatory cytokine release, and focal lymphocytic infiltration (ie, mainly $CD4^+$ T cells but also B cells) of the lacrimal and salivary gland, with glandular degeneration and induction of apoptosis in the conjunctiva and lacrimal glands. This results in dysfunction of the lacrimal gland, with reduced tear production, and loss of response to nerve stimulation and less reflex tearing. Active T lymphocytic infiltrate in the conjunctiva also has been reported in non-SS associated KCS.

Both androgen and estrogen receptors are located in the lacrimal and meibomian glands. SS is more common in postmenopausal women. At menopause, a decrease in circulating sex hormones (ie, estrogen, androgen) occurs, possibly affecting the functional and secretory aspect of the lacrimal gland. Forty years ago, initial interest in this area centered on estrogen and/or progesterone deficiency to explain the link between KCS and menopause. However, recent research has focused on androgens, specifically testosterone, and/or metabolized androgens.

It has been shown that in meibomian gland dysfunction, a deficiency in androgens results in loss of the lipid layer, specifically triglycerides, cholesterol, monounsaturated essential fatty acids (eg, oleic acid), and polar lipids (eg, phosphatidylethanolamine, sphingomyelin). The loss of polar lipids (present at the aqueous-tear interface) exacerbates the evaporative tear loss, and the decrease in unsaturated fatty acids raises the melting point of meibum, leading to thicker, more viscous secretions that obstruct ductules and cause stagnation of secretions. Patients on anti-androgenic therapy for prostate disease also have increased viscosity of meibum, decreased tear break-up time, and increased tear film debris, all indicative of a deficient or abnormal tear film.

It is known that in various tissues pro-inflammatory cytokines may cause cellular destruction. For example including interleukin 1 (IL-1), interleukin 6 (IL-6), interleukin 8 (IL-8), TGF-beta, TNF-alpha, and RANTES, are altered in patients with KCS. IL-1 beta and TNF-alpha, which are present in the tears of patients with KCS, cause the release of opioids that bind to opioid receptors on neural membranes and inhibit neurotransmitter release through NF-K β production. IL-2 also binds to the delta opioid receptor and inhibits cAMP production and neuronal function. This loss of neuronal function diminishes normal neuronal tone, leading to sensory isolation of the lacrimal gland and eventual atrophy.

Pro-inflammatory neurotransmitters, such as substance P and calcitonin gene related peptide (CGRP), are released, which recruit and activate local lymphocytes. Substance P also acts via the NF-AT and NF-K β signaling pathway leading to ICAM-1 and VCAM-1 expression, adhesions molecules that promote lymphocyte homing and chemotaxis to sites of inflammation. Cyclosporin A is an NK-1 and NK-2 receptor inhibitor that can down-regulate these signaling molecules and is a novel addition to the therapeutic armamentarium for dry eye, being used to treat both aqueous tear deficiency and meibomian gland dysfunction. It has been shown to improve the goblet cell counts and to reduce the numbers of inflammatory cells and cytokines in the conjunctiva.

These pro-inflammatory cytokines, in addition to inhibiting neural function, may also convert androgens into estrogens, resulting in meibomian gland dysfunction, as discussed above. An increased rate of apoptosis is also seen in conjunctival and lacrimal acinar cells, perhaps due to the cytokine cascade. Elevated levels of tissue-degrading enzymes called matrix metalloproteinases (MMPs) are also present in the epithelial cells.

Mucin synthesizing genes, designated MUC1-MUC17, representing both transmembrane and goblet-cell secreted, soluble mucins, have been isolated, and their role in hydration and stability of the tear film are being investigated in patients with dry eye syndrome. Particularly significant is MUC5AC, expressed by stratified squamous cells of the conjunctiva and whose product is the predominant component of the mucous layer of tears. A defect in this and other mucin genes may be a factor in dry eye syndrome development. In addition to dry eye, other conditions, such as ocular cicatricial pemphigoid, Stevens-Johnson syndrome, and vitamin A deficiency, which lead to drying or keratinization of the ocular epithelium, eventually lead to goblet cell loss. Both classes of mucins are decreased in these diseases, and, on a molecular level, mucin gene expression, translation, and posttranslational processing are altered.

Normal production of tear proteins, such as lysozyme, lactoferrin, lipocalin, and phospholipase A2, is decreased in KCS.

It is clear from the above discussion that common causes of dry eye syndromes may be ameliorated by treatment with anti-inflammatory agents such as topical corticosteroids, topical cyclosporine A and/or topical/systemic omega-3 fatty acids.

Dry Eye References

Basic teachings regarding dry eye can be found in the following references:
Dry Eye Workshop (DEWS) Committee. 2007 Report of the Dry Eye Workshop (DEWS). *Ocul Surf.* April 2007; 5(2):65-204.
Behrens A, Doyle J J, Stern L, et al. Dysfunctional tear syndrome: a Delphi approach to treatment recommendations. *Cornea.* September 2006; 25(8):900-7. [Medline].
Abelson M B. Dry eye, today and tomorrow. *Review in Ophthalmology.* 2000; 11:132-34.

American Academy of Ophthalmology. External disease and cornea. In: *Section Seven: Basic & Clinical Science Course.* American Academy of Ophthalmology; 2007-2008.

Barabino S, Rolando M, Camicione P, et al. Systemic linoleic and gamma-linolenic acid therapy in dry eye syndrome with an inflammatory component. *Cornea.* March 2003; 22(2):97-101. [Medline].

Bron A J, Tiffany J M, Gouveia S M, et al. Functional aspects of the tear film lipid layer. *Exp Eye Res.* March 2004; 78(3):347-60. [Medline].

Geerling G, Maclennan S, Hartwig D. Autologous serum eye drops for ocular surface disorders. *Br J Ophthalmol.* November 2004; 88(11):1467-74. [Medline].

Gilbard J P. Dry eye disorders. In: Albert D M, Jakobiec F A, eds. *Principles and Practice of Ophthalmology.* Vol 2. WB Saunders Co; 2000:982-1000.

Karadayi K, Ciftci F, Akin T, et al. Increase in central corneal thickness in dry and normal eyes with application of artificial tears: a new diagnostic and follow-up criterion for dry eye. *Ophthalmic Physiol Opt.* November 2005; 25(6):485-91. [Medline].

McCulley J P, Shine W E. The lipid layer of tears: dependent on meibomian gland function. *Exp Eye Res.* March 2004; 78(3):361-5. [Medline].

Murube J, Nemeth J, Hoh H, et al. The triple classification of dry eye for practical clinical use. *Eur J Ophthalmol.* November-December 2005; 15(6):660-7. [Medline].

Ohashi Y, Dogru M, Tsubota K. Laboratory findings in tear fluid analysis. *Clin Chim Acta.* Jul. 15, 2006; 369(1):17-28. [Medline].

Perry H D, Donnenfeld E D. Dry eye diagnosis and management in 2004. *Curr Opin Ophthalmol.* August 2004; 15(4): 299-304. [Medline].

Pflugfelder S C. Advances in the diagnosis and management of keratoconjunctivitis sicca. *Curr Opin Ophthalmol.* August 1998; 9(4):50-3. [Medline].

Stern M E, Gao J, Siemasko K F, et al. The role of the lacrimal functional unit in the pathophysiology of dry eye. *Exp Eye Res.* March 2004; 78(3):409-16. [Medline].

Tatlipinar S, Akpek E K. Topical ciclosporin in the treatment of ocular surface disorders. *Br J Ophthalmol.* October 2005; 89(10):1363-7. [Medline].

Yoon K C, Heo H, Im S K, et al. Comparison of autologous serum and umbilical cord serum eye drops for dry eye syndrome. *Am J Ophthalmol.* July 2007; 144(1):86-92. [Medline].

Zoukhri D. Effect of inflammation on lacrimal gland function. *Exp Eye Res.* May 2006; 82(5):885-98. [Medline].

Associated AMD References

Associated AMD teachings can be found in the following references:

1) Macular Photocoagulation Study Group: Argon Laser Photocoagulation for senile macular degeneration: Results of a randomized clinical trial. *Arch Ophthalmol,* 1982; 100: 912-918.
2) TAP study group. Photodynamic therapy of subfoveal choroidal neovascularization in age-related macular degeneration with verteporfin. One-year results of 2 randomized clinical trials—TAP report 1. *Arch Ophthalmol,* 1999; 117: 1329-1345.
3) Gragoudas E S, Adamis A P, Cunningham E T, et al. Pegaptanib for Neovascular Age-Related Macular Degeneration. *NEJM,* 2004; 351:2805-2816.
4) Michels S, Rosenfeld P J. Treatment of neovascular age-related macular degeneration with Ranibizumab/Lucentis. *Klin Monatsbl Augenheilkd,* 2005; 222(6):480-484.
5) Kini M M, Leibowitz H M, Colton T, et al. Prevalence of senile cataract, diabetic retinopathy, senile macular degeneration, and open-angle glaucoma in the Framingham Eye Study. *Am J Ophthalmol,* 1978; 85:28-34.
6) Smiddy W E, Fine S L. Prognosis of patients with bilateral macular drusen. *Ophthalmol,* 1984; 91:271-277.
7) Friedman D S, O'Colmain B J, Munoz B, et al. (Eye Disease Prevalence Research Group.) Prevalence of age-related macular degeneration in the United States. *Arch Ophthalmol,* 2004; 122:564-572.
8) Age-Related Eye Disease Study Research Group. A randomized, placebo-controlled, clinical trial of high-dose supplementation with vitamins C and E, beta-carotene, and zinc for age-related macular degeneration and vision loss: AREDS Report No. 8. *Arch Ophthalmol,* 2001; 119:1417-36.
9) Dietary Reference Intakes for Vitamin C, Vitamin E, Selenium, and Carotenoids. Washington, D.C.: Academy Press; 2000.
10) Khachik F, Spangler C J, Smith J C, Jr., Canfield L M, Steck A, Pfander H. Identification, quantification, and relative concentrations of carotenoids and their metabolites in human milk and serum. *Anal Chem,* 1997; 69(10):1873-1881.
11) Bone R A, Landrum J T, Tarsis S L. Preliminary identification of the human macular pigment. *Vision Res,* 1985; 25(11):1531-1535.
12) Chew E Y, SanGiovanni J P. Lutein. *Encyclopedia of Dietary Supplements,* pp. 409-420, Marcel Dekker, Inc., 2005.
13) SanGiovanni J P, Chew E Y. The role of omega-3 long-chain polyunsaturated fatty acids in health and disease of the retina. *Progress in Retinal and Eye Research,* 2005; 24:87-138.
14) Neuringer M. in Lipids, Learning, and the Brain: Fats in Infant Formulas, 103*rd Ross Conference on Pediatric Research* (ed. Dabbing, J.), 1993, 134-158 (Ross Laboratories, Adeliade, South Australia).
15) Fliesler S J, Anderson R E. Chemistry and metabolism of lipids in the vertebrate retina. *Prog Lipid Res,* 1983; 22:79-131.
16) Litman B J, Mitchell D C. A role for phospholipid polyunsaturation in modulating membrane protein function. *Lipids,* 1996; 31(Suppl):S193-7.
17) Litman B J, Niu S L, Polozova A, Mitchell D C. The role of docosahexaenoic acid containing phospholipids in modulating G protein-coupled signaling pathways: Visual transduction. *J Mol Neurosci,* 2001; 16(2-3):237-242; discussion 279-284.
18) Schaefer E J, Robins S J, Patton G M, et al. Red blood cell membrane phosphatidylethanolamine fatty acid content in various forms of retinitis pigmentosa. *J Lipid Res,* 1995; 36(7):1427-1433.
19) Hoffman D R, Birch D G. Docosahexaenoic acid in red blood cells of patients with X-linked retinitis pigmentosa. *Invest Ophthalmol Vis Sci,* 1995; 36(6):1009-1018.
20) Hoffman D R, Uauy R, Birch D G. Metabolism of omega-3 fatty acids in patients with autosomal dominant retinitis pigmentosa. *Exp Eye Res,* 1995; 60(3):279-289.
21) Martinez M, Vazquez E, Garcia-Silva M T, et al. Therapeutic effects of docosahexaenoic acid ethyl ester in patients with generalized peroxisomal disorders. *Am J Clin Nutr,* 2000; 71(1 Suppl):376S-385S.

22) Jumpsen J, M. T. C. *Brain Development: Relationship to Dietary Lipid and Lipid Metabolism.* 1997; Champaign, Ill.: AOCS Press.
23) Clandinin M T, Jumpsen J, Suh M. Relationship between fatty acid accretion, membrane composition, and biologic functions. *J Pediatr,* 1994; 125(5 Pt 2):S25-32.
24) Salem N, Jr., Litman B, Kim H Y, Gawrisch K. Mechanisms of action of docosahexaenoic acid in the nervous system. *Lipids,* 2001; 36(9):945-959.
25) Chen Y, Houghton L A, Brenna J T, Noy N. Docosahexaenoic acid modulates the interactions of interphotoreceptor retinoid-binding protein with 11-cis-retinal. *J Biol Chem,* 1996; 271(34):20507-20515.
26) de Urquiza, A M et al. Docosahexaenoic acid, a ligand for the retinoid X receptor in mouse brain. *Science,* 2000; 290:2140-4.
27) Lin Q, Ruuska S E, Shaw N S, dong D, Noy N. Ligand selectivity of the peroxisome proliferator-activated receptor alpha. *Biochemistry,* 1999; 38:185-90.
28) Dreyer C, et al. Positive regulation of the peroxisomal beta-oxidation pathway by fatty acids through activation of peroxisome proliferator-activated receptors (PPAR). *Biol Cell,* 1993; 77:67-76.
29) Yu K, et al. Differential activation of peroxisome proliferator-activated receptors by eicosanoids. *J Biol Chem,* 1995; 270:23975-83.
30) Politi L E, Rotstein N P, Carri N G. Effect of GDNF on neuroblast proliferation and photoreceptor survival: additive protection with docosahexaenoic acid. *Invest Ophthalmol Vis Sci,* 2001; 42(12):3008-3015.
31) Rotstein N P, Aveldano M I, Barrantes F J, Roccamo A M, Politi L E. Apoptosis of retinal photoreceptors during development in vitro: protective effect of docosahexaenoic acid. *J Neurochem,* 1997; 69(2):504-513.
32) Rotstein N P, Politi L E, Aveldano M I. Docosahexaenoic acid promotes differentiation of developing photoreceptors in culture. *Invest Ophthalmol Vis Sci,* 1998; 39(13): 2750-2758.
33) Rotstein N P, Aveldano M I, Barrantes F J, Politi L E. Docosahexaenoic acid is required for the survival of rat retinal photoreceptors in vitro. *J Neurochem,* 1996; 66(5): 1851-1859.
34) Kim H Y, Akbar M, Kim K Y. Inhibition of neuronal apoptosis by polyunsaturated fatty acids. *J Mol Neurosci,* 2001; 16(2-3):223-227; discussion 279-284.
35) Diep Q N, Amiri F, Youyz R M, et al. PPARalpha activator effects on Ang II-induced vascular oxidative stress and inflammation. *Hypertension,* 2002; 40(6):866-871.
36) Yang S P, Morita I, Murota S I. Eicosapentaenoic acid attenuates vascular endothelial growth factor-induced proliferation via inhibiting Flk-1 receptor expression in bovine carotid artery endothelial cells. *J Cell Physiol,* 1998; 176(2):342-349.
37) von Knethen A, Callsen D, Brune B. Superoxide attenuates macrophage apoptosis by NF-kappa B and AP-1 activation that promotes cyclooxygenase-2 expression. *J Immunol,* 1999; 163(5):2858-2866.
38) Morita I, Zhang Y W, Murata S I. Eicosapentaenoic acid protects endothelial cell function injured by hypoxia/reoxygenation. *Ann NY Acad Sci,* 2001; 947:394-397.
39) Calder P C. Polyunsaturated fatty acids, inflammation, and immunity. *Lipids,* 2001; 36(9): 1007-1024.
40) Rose D P, Connolly J M, Rayburn J, Coleman M. Influence of diets containing eicosapentaenoic or docosahexaenoic acid on growth and metastasis of breast cancer cells in nude mice. *J Natl Cancer Inst,* 1995; 87(8):587-592.
41) Rose D P, Connolly J M. Antiangiogenicity of docosahexaenoic acid and its role in the suppression of breast cancer cell growth in nude mice. *Int J Oncol,* 1999; 15(5): 1011-1015.
42) Badawi A F, El-Sohemy A, Stephen L L, Ghoshal A K, Archer M C. The effect of dietary n-3 and n-6 polyunsaturated fatty acids on the expression of cyclooxygenase 1 and 2 and levels of p21as in rat mammary glands. *Carcinogenesis,* 1998; 19(5):905-910.
43) Hamid R, Singh J, Reddy B S, Cohen L A. Inhibition of dietary menhaden oil of cyclooxygenase-1 and -2 in N-nitrosomethylurea-induced rat mammary tumors. *Int J Oncol,* 1999; 14(3):523-528.
44) Ringbom T, Huss U, Stenholm A, et al. Cox-2 inhibitory effects of naturally occurring and modified fatty acids. *J Nat Prod,* 2001; 64(6):745-749.
45) Kanayasu T, Morita I, Nakao-Hayashi J, et al. Eicosapentaenoic acid inhibits tube formation of vascular endothelial cells in vitro. *Lipids,* 1991; 26(4):271-276.
46) Farrara N, Davis-Smyth T. The biology of vascular endothelial growth factor. *Endocr Rev,* 1997; 18(1):4-25.
47) Mares-Perlman J A, Brady W E, Klein R, VandenLangenberg G M, Klein B E, Plata M. Dietary fat and age-related maculopathy. *Arch Ophthalmol,* 1995; 113(6):743-8.
48) Heuberger R A, Mares-Perlman J A, Klein R, Klein B E, Millen A E, Palta M. Relationship of dietary fat to age-related maculopathy in the Third National Health and Nutrition Examination Survey. *Arch Ophthalmol,* 2001; 119(12):1833-8.
49) Smith W, Mitchell P, Leeder S R. Dietary fat and fish intake and age-related maculopathy. *Arch Ophthalmol,* 2000; 118(3):401-4.
50) Seddon J M, Rosner B, Sperduto R D, Yannuzzi L, Haller J A, Blair N P, Willett W. Dietary fat and risk for advanced age-related macular degeneration. *Arch Ophthalmol,* 2001; 119(8):1191-9.
51) Seddon J M, Cote J, Rosner B. Progression of age-related macular degeneration: Association with dietary fat, transunsaturated fat, nuts, and fish intake. *Arch Ophthalmol,* 2003; 121(12):1728-1737.
52) SanGiovanni J P, Chew E Y, Clemons T E, Seddon J M, Klein R, Age-Related Eye Disease Study (AREDS) Research Group. Dietary lipids intake and incident advanced Age-Related Macular Degeneration (AMD) in the Age-Related Eye Disease Study (AREDS). Annual Meeting, May 2005, Association for Research in Vision and Ophthalmology (ARVO), Fort Lauderdale, Fla.
53) Seddon J M, Ajani D A, Sperduto R D, et al. Dietary carotenoids, vitamins A, C and E, and advanced age-related macular degeneration. Eye Disease Case-Control Study Group. *JAMA,* 1994; 272(18):1413-20.
54) Snellen E L, Verbeek A L, Van Den Hoogen G W, Cruysberg J R, Hoyng C B. Neovascular age-related macular degeneration and its relationship to antioxidant intake. *Acta Ophthalmol Scand,* 2002; 80(4):368-71.
55) Mares-Perlman J A, Fisher A I, Klein R, et al. Lutein and zeaxanthin in the diet and serum and their relation to age-related maculopathy in the Third National Health and Nutrition Examination Survey. *Am J Epidemiol,* 2001; 153 (5):424-32.
56) Mares-Perlman J A, Klein R, Klein B E, et al. Association of zinc and antioxidant nutrients with age-related maculopathy. *Arch Ophthalmol,* 1996; 114(8):991-7.
57) Age-Related Eye Disease Study Research Group. The relationship of dietary carotenoids, vitamin A, E and C intake with age-related macular degeneration. A case-control study in the Age-Related Eye Disease Study: submitted to *Arch Ophthalmol.*
58) Cho E, Seddon J M, Rosner B, Willett W C, Hankinson S E. Prospective study of intake of fruits, vegetables, vitamins, carotenoids and risk of age-related maculopathy. *Arch Ophthalmol,* 2004; 122(6):883-892.
59) Lan K K G, Lachin J M. Implementation of group sequential logrank tests in a maximum duration trial. *Biometrics,* 1990; 46:759-770.
60) Lan K K G, DeMets D L. Discrete sequential boundaries for clinical trials. *Biometrika,* 1983; 70:659-663.
61) O'Brien P C, Fleming T R. A multiple testing procedure for clinical trials. *Biometrics,* 1979; 35:549-556.
62) Liang K Y, Zeger S L. Longitudinal data analysis using generalized linear models. *Biometrika,* 1986; 73:13-22.
63) Miller E R, Pastor-Barriuso R, Darshan D, Riemersma R A, Appel L J, Guallar E. Meta-analysis: high-dosage vitamin E supplementation may increase all-cause mortality. *Ann Intern Med.* 2005; 143:37-46.
64) Parisi et al. Carotenoids and antioxidants in age related maculopathy study. *Ophthalmology* 2008; 115; 324-333.
65) Tso, U.S. Pat. No. 5,533,527.
66) Deutsch et al., Evaluation of the effects of Neptune krill oil on chronic inflammation and arthritis symptoms, *Journal of the American College of Nutrition,* Vol 26, No. 1, 39-48 (2007).
67) Bunea et al. Evaluation of the effects of Neptune krill oil on the clinical course of hyperlipidemia, *Alternative Medicine Review,* 9(4):420-428 (2004).
68) Eslick et al. Benefits of fish oil supplementation in hyperlipidemia: a systematic review and meta analysis. *Int. J. Cardiology* 2009; 136:4-16.
69) Hu et al. Types of dietary fat and risk of coronary heart disease: A critical review. *J. Am. Coll. Nutrition* 2001:20: 5-19.
70) Kris-Etherton et al. *Curr. Atheroscler. Report* 2008; 10:503-509.
71) Breslow J. N-3 fatty acids and cardiovasualr disease *Am. J. Clin. Nutrition* 2006; 83(suppl):1477S-82S.
72) Leaf et al. Prevention of sudden death by omega-3 polyunsaturated fatty acids. *Pharmacol. Therapy* 2003; 98:355-77.
73) Maki et al. Krill oil supplementation increases plasma concentrations of eicosapentaenoic and docosahexaenoic acids in overweight and obese men and women. *Nutrition Research* 29; (2009):609-15.
74) Massrieh, W. Health benefits of omega-3 fatty acids from Neptune Krill oil. *Lipid Technology*, May 2008, Vol 20, No. 5.
75) See: http://emedicine.medscape.com/article/1210417-overview.

Five of six studies examining the association of dietary lutein/zeaxanthin intake with advanced AMD have yielded inverse relationships that are statistically significant. The magnitude of odds ratios in these studies ranged from 0.1 to 0.7. Both sets of findings are germane in guiding applied clinical research on prevention and treatment of retinal disease, since: (1) tissue concentrations of DHA, lutein, and zeaxanthin per unit area are substantially higher in the retina than elsewhere in the body; and (2) retinal tissue status of these compounds is modifiable and dependent upon intake.

The AREDS II study protocol (concluded its scientific rational by stating: "There is a compelling need to implement a clinical trial on nutrients that are both concentrated in the retina and implicated in modulation of pathogenic factors and processes of AMD."

It has been well established that lutein and trans-zeaxanthin are present in human retinal tissue and that they function to protect the eye from photo induced injury. The CARMIS study, which included a mixture of lutein, trans-zeaxanthin and astaxanthin, is the only clinical trial which reported the use of astaxanthin. Unfortunately, there have been no reports of the use of astaxanthin alone in any human clinical trial for the prevention or amelioration of dry AMD. The CARMIS study failed to determine if supplementation with astaxanthin alone is a key determinate of the positive outcomes of the study or that astaxanthin deposited on retinal epithelial cells. One possible interpretation of the CARMIS study is that lutein and zeaxanthin alone provided the observed benefits of the formulation employed, or in another interpretation that astaxanthin in combination with lutein and zeaxanthin provided the observed benefits. However, in no possible interpretation can one conclude unequivocally that astaxanthin alone prevents or ameliorates dry AMD.

In addition, the work of Tso, though claiming utility of astaxanthin for prevention or amelioration of dry AMD in humans, was not based on clinical trials performed on human subjects but instead on a different mammalian species, namely in rats.

Therefore, there remains no conclusive evidence that astaxanthin alone can prevent or ameliorate dry AMD in man since no human study has ever been performed using astaxanthin supplementation alone, nor has any human study shown that astaxanthin actually deposits anywhere in the human retina, the first required step to retinal protection by this powerful carotenoid.

Potential Roles of Polyunsaturated Fatty Acids in Eye Physiology

An inverse relationship of dietary omega-3 LCPUFA intake with advanced AMD has been reported in six studies examining the issue. For prevalent disease, the magnitude of odds ratios for highest versus lowest omega-3 LCPUFA intake ranged from 0.4 to 0.9.

Among these studies, the one containing the largest number of subjects with neovascular or "wet" AMD yielded a significantly lower likelihood of having the disease among participants reporting the highest consumption of omega-3.

The scientific literature is replete with the certain human benefits of triacylglyceride bound EPA and DHA found in fish oil and fish oil concentrates and more recently the potential utility of phospholipid bound EPA and DHA found in krill oil derived from *Euphasia superba* or Antarctic krill.

The cardiovascular benefits as well as the anti-inflammatory benefits of such fish and krill oils[66-67], and in particular triacylglyceride bound EPA and DHA derived from fish oils as well as algae derived triacylglyceride bound DHA are well known[68-73]. Such algae derived DHA is used in large part as a supplement in infant formulas to ensure brain health in the developing fetus and in infants.

LCPUFAs affect factors and processes implicated in the pathogenesis of vascular and neural retinal disease.[13] Evidence characterizing structural and functional properties of LCPUFAs indicates that these nutrients may operate both as: (1) essential factors in the visual-sensory process, and (2) protective agents against retinal disease.

Docosahexaenoic Acid (DHA) is the major structural lipid of retinal photoreceptor outer segment membranes.[14-15] Tissue DHA status affects retinal cell signaling mechanisms involved in phototransduction.[16-17] Tissue DHA insufficiency is associated with conditions characterized by alterations in retinal function,[18-20] and functional deficits have been ameliorated with DHA supplementation in some cases.[21] Biophysical and biochemical properties of DHA may affect photoreceptor function by altering membrane permeability, fluidity, thickness, and lipid phase properties.[22-23] DHA may operate in signaling cascades to enhance activation of membrane-bound retinal proteins.[16-17,24] DHA may also be involved in rhodopsin regeneration.[25]

DHA and Eicosapentaenoic Acid (EPA) may serve as protective agents because of their effect on gene expression,[26-29] retinal cell differentiation,[30-32] and survival.[30-34] DHA activates a number of nuclear hormone receptors that operate as transcription factors for molecules that modulate redox-sensitive and proinflammatory genes; these include the peroxisome proliferator-activated receptor-α (PPAR-α)[27] and the retinoid X receptor (RXR).[26] In the case of PPAR-α, this action is thought to prevent endothelial cell dysfunction and vascular remodeling through inhibition of vascular smooth muscle cell proliferation, inducible nitric oxide synthase production, interleukin (IL)-1 induced cyclooxygenase (COX)-2 production, and thrombin-induced endothelin-1 production.[35]

Research on model systems demonstrates that omega-3 LCPUFAs also have the capacity to affect production and activation of angiogenic growth factors,[36-38] arachidonic acid-based proangiogenic eicosanoids,[39-43] and matrix metalloproteinases involved in vascular remodeling.[44]

EPA depresses vascular endothelial growth factor (VEGF)-specific tyrosine kinase receptor activation and expression.[36,45] VEGF plays an essential role in induction of endothelial cell migration and proliferation, microvascular permeability, endothelial cell release of metalloproteinases and interstitial collagenases, and endothelial cell tube formation.[46] The mechanism of VEGF receptor down-regulation is believed to occur at the tyrosine kinase nuclear factor-kappa B (NFkB) site because EPA treatment causes suppression of NFkB activation. NFkB is a nuclear transcription factor that up-regulates COX-2 expression, intracellular adhesion molecule (ICAM), thrombin, and nitric oxide synthase. All four factors are associated with vascular instability.[35] COX-2 drives conversion of arachidonic acid to a number of angiogenic and pro-inflammatory eicosanoids.

Although the mechanistic benefits of dietary supplementation with EPA and DHA polyunstaruated fatty acids in triacylglyceride form are well know, it remains speculative that such triacylglyceride bound EPA and DHA can improve vision. Such hypothesis is now under exploration under the National Eye Institute's 5-year AREDS II study.

Krill Oil

Nowhere does the literature teach that phospholipid bound EPA and DHA derived from Antarctic krill imparts any benefit in ameliorating eye related diseases such as AMD and/or syndromes such as dry eye syndrome, although more recent research indicates that krill oil extracts containing some phospholipid bound EPA and DHA may be useful in the treatment of hyperlipidemia, joint disease as manifested in osteoarthritis and/or rheumatoid arthritis, blood sugar control and attention deficit hyperactivity disorder.[74]

However one must use caution when evaluating such information since all krill oil clinical trials to date have been conducted using krill oil that contains a mixture of triacylglyceride bound and phospholipid bound EPA and DHA. In addition, such krill oils usually contain approximately 30-40% weight-weight phospholipid bound fatty acids, principally in the form of saturated phosphatidylcholines which themselves are important cellular membrane components.

Thus, it is difficult at the present time, to distinguish which form of EPA and DHA present in krill oil is useful as reported in the references cited above as well as the clinical trials described therein. It is also well known that phospholipids in general act as excellent emulsifiers and are known to improve the stability of emulsions and the bio-availability of many active ingredients. Phospholipids also play an important role in the production of micelle based drug delivery systems containing active ingredients with vastly improved bio-availability. Therefore it remains undetermined what the clinical value of krill oil, either alone or in combination with carotenoids, is in the prevention or amelioration of eye related diseases such as AMD, cataracts or dry eye syndromes.

Cataracts

A cataract is an opacity, or clouding, of the lens of the eye. The prevalence of cataracts increases dramatically with age. It typically occurs in the following way. The lens is an elliptical structure that sits behind the pupil and is normally transparent. The function of the lens is to focus light rays into images on the retina (the light-sensitive tissue at the back of the eye).

In young people, the lens is elastic and changes shape easily, allowing the eyes to focus clearly on both near and distant objects. As people reach their mid-40s, biochemical changes occur in the proteins within the lens, causing them to harden and lose elasticity. This causes a number of vision problems. For example, loss of elasticity causes presbyopia, or far-sightedness, requiring reading glasses in almost everyone as they age.

In some people, the proteins in the lens, notably those called alpha crystallins, may also clump together, forming cloudy (opaque) areas called cataracts. They usually develop slowly over several years and are related to aging. In some cases, depending on the cause of the cataracts, loss of vision progresses rapidly. Depending on how dense they are and where they are located, cataracts can block the passage of light through the lens and interfere with the formation of images on the retina, causing vision to become cloudy.

Nuclear cataracts form in the nucleus (the inner core) of the lens. This is the most common variety of cataract associated with the aging process. Cortical cataracts form in the cortex (the outer section of the lens). Posterior subcapsular cataracts form toward the back of a cellophane-like capsule that surrounds the lens. They are more frequent in people with diabetes, who are overweight, or those taking steroids. Although the causes of cataract formation remain largely unknown, researchers have been focusing on particles called oxygen-free radicals as a major factor in the development of cataracts. They cause harm in the following way:

Oxygen-free radicals (also called oxidants) are molecules produced by natural chemical processes in the body. Toxins, smoking, ultraviolet radiation, infections, and many other factors can create reactions that produce excessive amounts of these oxygen-free radicals. When oxidants are overproduced, these chemical reactions can be very harmful to nearly any type of cell in the body. At times these reactions can even affect genetic material in cells.

Cataract formation is one of many destructive changes that can occur with overproduction of oxidants, possibly in concert with deficiencies of an important protective antioxidant called glutathione. Glutathione occurs in high levels in the eye and helps clean up these free radicals. One theory is that in the aging eye, barriers develop that prevent glutathione and other protective antioxidants from reaching the nucleus in the lens, thus making it vulnerable to oxidation. Sunlight consists of ultraviolet (referred to as UVA or UVB) radiation, which penetrates the layers of the skin. Both UVA and UVB have destructive properties that can promote cataracts. The eyes are protected from the sun by eyelids and the structure of the face (overhanging brows, prominent cheekbones, and the nose). Long-term exposure to sunlight, however, can overcome these defenses.

UVB radiation produces the shorter wavelength, and primarily affects the outer skin layers. It is the primary cause of sunburn. It is also the UV radiation primarily responsible for cataracts. Long-term exposure to even low levels of UVB radiation can eventually cause changes in the lens, including pigment changes, which contribute to cataract development. (UVB also appears to play a role in macular degeneration, an age-related disorder of the retina.) UVA radiation is composed of longer wavelengths. They penetrate more deeply and efficiently into the inner skin layers and are responsible for tanning. The main damaging effect of UVA appears to be the promotion of the release of oxidants. Cataracts are common side effects of total body radiation treatments, which are administered for certain cancers. This observation indicates that ionizing radiation, which produces large numbers of free radicals dramatically accelerates cataract formation.

Glaucoma and its treatments, including certain drugs (notably miotics) and filtering surgery, pose a high risk for cataracts. The glaucoma drugs posing a particular risk for cataracts including demecarium (Humorsol), isoflurophate (Floropryl), and echothiophate (Phospholine). Uveitis is chronic inflammation in the eye, which is often caused by an autoimmune disease or response. Often the cause is unknown. It is a rare condition that carries a high risk for cataracts. It is not clear whether nutrition plays a significant role in cataract development. Dark colored (green, red, purple, and yellow) fruits and vegetables usually have high levels of important plant chemicals (phytochemicals) and may be associated with a lower risk for cataracts.

In analyzing nutrients, researchers have focused on antioxidants and carotenids. Studies have not demonstrated that antioxidant vitamin supplements (such as vitamins C and E) help prevent cataracts. Lutein and zeaxanthin are the two carotenids that have been most studied for cataract prevention. They are xanthophylis compounds, which are a particular type of carotenid. Lutein and zeaxanthin are found in the lenses of the eyes. Some evidence indicates that xanthophyll-rich foods (such as dark green leafy vegetables) may help retard the aging process in the eye and protect against cataracts. However, there is not enough evidence to suggest that taking supplements with these carotenoids lowers the risk of cataract formation. Since little is known about the exact mechanism for formation of cataracts, it is not surprising that there are no known drugs or dietary supplements including the carotenoids that prevent cataract formation there remains a need to find a suitable preventative treatment to prevent or ameliorate further cataract formation. Since no drugs can reverse nor prevent cataract formation, the only current treatment suitable for advanced cataract in humans is lens replacement surgery.

Cataract References

Basic teachings regarding cataracts can be found in the following references:

Allen D. *Cataract. BMJ Clinical Evidence*. Web publication date: 1 Apr. 2007 (based on October 2006 search). Accessed Jul. 1, 2008.

American Academy of Ophthalmology. *Cataract in the Adult Eye, Preferred Practice Pattern*. San Francisco: American Academy of Ophthalmology, 2006. Accessed Jul. 1, 2008.

Awasthi N, Guo S, Wagner B J. Posterior capsular opacification: a problem reduced but not yet eradicated. *Arch Ophthalmol*. 2009 April; 127(4):555-62.

Bell C M, Hatch W V, Fischer H D, Cernat G, Paterson J M, Gruneir A, et al. Association between tamsulosin and serious ophthalmic adverse events in older men following cataract surgery. *JAMA*. 2009 May 20; 301(19):1991-6

Clinical Trial of Nutritional Supplements and Age-Related Cataract Study Group, Maraini G, Sperduto R D, Ferris F. Clemons T E, Rosmini F, et al. A randomized, double-masked, placebo-controlled clinical trial of multivitamin supplementation for age-related lens opacities. Clinical trial of nutritional supplements and age-related cataract report no. 3. *Ophthalmology*. 2008 April; 115(4):599-607.e1.

Fernandez M M, Afshari N A. Nutrition and the prevention of cataracts. *Curr Opin Ophthalmol*. 2008 January; 19(1):66-70.

Friedman A H. Tamsulosin and the intraoperative floppy iris syndrome. *JAMA*. 2009 May 20; 301(19):2044-5.

Guercio J R, Martyn L J. Congenital malformations of the eye and orbit. *Otolaryngol Clin North Am*. 2007 February; 40(1):113-40, vii.

Long V, Chen S, Hatt S. Surgical interventions for bilateral congenital cataract. *Cochrane Database Syst Rev*. 2006 Jul. 19; 3:CD003171.

Moeller S M, Voland R, Tinker L, Blodi B A, Klein M L, Gehrs K M, et al. Associations between age-related nuclear cataract and lutein and zeaxanthin in the diet and serum in the Carotenoids in the Age-Related Eye Disease Study, an Ancillary Study of the Women's Health Initiative. *Arch Ophthalmol*. 2008 March; 126(3):354-64.

Olitsky S E, Hug D, and Smith L P. Abnormalities of the lens. In: Kliegman R M, Behrman R E, Jenson H B, Stanton B F, eds. *Nelson Textbook of Pediatrics*. 18th ed. St. Louis, Mo.: WB Saunders; 2007; chap 627.

Wishart M S, Dagres E. Seven-year follow-up of combined cataract extraction and viscocanalostomy. *J Cataract Refract Surg*. 2006 December; 32(12):2043-9.

The ability of a carotenoid to pass the blood-retinal brain barrier is important because carotenoids are not synthesized by the human body. The only source of carotenoids for humans is dietary intake. Furthermore, humans have a very limited ability to modify carotenoids. Therefore, the carotenoids accumulate in various organs in the ingested form. Accordingly, if a particular carotenoid is unable to cross the blood-retinal brain barrier, the carotenoid cannot accumulate in the retina and serve as an antioxidant.

Furthermore, some carotenoids that are not normal constituents of human plasma, but have the ability to cross the blood-retinal brain barrier, have demonstrated adverse affects on the retina. Canthaxanthin which is intentionally ingested to provide an artificial suntan has accumulated in the retina in the form of crystals and has temporarily affected eye adaptation to the dark. In addition, beta-carotene has a very limited ability to cross the blood-retinal brain barrier.

Therefore, even though the carotenoids are known as strong antioxidants and are present in abundant supply, the carotenoids have not been used for the treatment of central nervous system damage, or eye damage, caused by disease or injury. The carotenoids investigated to date either could not effectively cross the blood-retinal barrier (i.e., beta-carotene) or adversely affected the eye (i.e., canthaxanthin).

In accordance with an important feature, the composition comprises a therapeutically effective amount of a synergistic multi-ingredient composition of mixed carotenoids including at least S,S'-astaxanthin derived from *Haematococcus pluvialis*, and one or more of lutein and/or trans-zeaxanthin or meso-zeaxanthin admixed with a therapeutically effective amount of krill oil containing phospholipid bound and triglyceride bound EPA and DHA. The composition includes 50 to 500 mg of krill oil, 0.5 to 8 mg of astaxanthin, 2 to 15 mg of lutein and 0.2 to 12 mg of trans-zeaxanthin. The composition contains all naturally-occurring compounds and is a potent antioxidant and anti-inflammatory composition, which can be is used in a method to ameliorate and retard, or prevent, cell damage in an individual suffering from a degenerative, inflammatory disease or injury to the eye. In accordance with another important feature, the administration of a therapeutically-effective amount of the composition to an individual prevents, retards and/or ameliorates free radical-induced damage resulting from eye disease or injury. For example, damage to a retina can result from either photic injury, neurodegenerative disease or an ischemic insult followed by reperfusion. With respect to damage from photic injury, the composition decreases the loss of photoreceptor cells. With respect to damage from ischemic insult, the composition ameliorates the loss of ganglion cells and the inner layers of the retinal neuronal network.

Interestingly, none of the carotenes tested to date, and most of the xanthophylls tested to date do not pass through the blood brain barrier with a few notable exceptions. These exceptions include lutein, trans-zeaxanthin, canthaxanthin and astaxanthin.

Human serum typically contains about ten carotenoids. The major carotenoids in human serum include beta-carotene, alpha-carotene, cryptoxanthin, lycopene and lutein. Small amounts of zeaxanthin, phytofluene and phytoene are also found in human organs. However, of all of these carotenoids, only zeaxanthin and lutein are found in the human retina. In addition to certain carotenoids, the retina also has the highest concentration of polyunsaturated fatty acids of any tissue in the human body. These polyunsaturated fatty acids are highly susceptible to free radial and singlet oxygen induced decomposition. Therefore there is an absolute need to protect these polyunsaturated fatty acids, which make up a portion of the cellular membrane bi-layer, from photo induced free radical or singlet oxygen degradation.

It has been theorized that zeaxanthin and lutein are concentrated in the retina because of their ability to quench singlet oxygen and to scavenge free radicals, because they pass the blood and eye brain barriers and are required in the oxygen rich environment of the retina to prevent light mediated free radical damage to the retina.

In fact, zeaxanthin is the predominant carotenoid found in the central portion of the retina and more specifically is located in concentration in the retinal cones located in the central area of the retina (ie. the macula). Lutein, on the other hand, is located in the peripheral area of the retina in the rod cells. Therefore, the eye preferentially accumulates zeaxanthin over lutein in the critical central macular retinal area, (zeaxanthin interestingly, is a much more effective singlet oxygen scavenger than lutein), where the greatest level of light impinges.

Biochemists have determined the exact, yet complicated, mechanism for light sensory response in the eye. It involves a key protein called rhodopsin whose structure includes a bound polyunsaturated compound called retinal (retinal is structurally related to vitamin A). When light enters the eye, cis-retinal isomerizes to all its all-trans isomer, causing dis-association of itself from its protein carrier. The disassociation triggers a complicated cascade leading to nerve based transmission of electrons to the brain via the optic nerve. All of this "photochemistry" takes a mere 200 femtoseconds to occur making it one of the fastest biochemical to electron transformations known.

Chemists have learned that the retina is highly susceptible to polymerization by localized free radicals and highly reactive singlet oxygen. Because the retina is a strong absorber of light and because the retina is highly vascularized and thus rich in dissolved oxygen, nature has provided zeaxanthin as the key retinal carotenoid for protection of the central foveal region of the retina from light induced damage at that point in the center of the retina where the most significant light impingement occurs.

Clinical studies in man indicate that photic injury is a cause of age related macular degeneration because of the cumulative effect of repeated photic insult leading to the gradual loss of photoreceptor cells.

There have been many clinical trials designed to support the supplementation of the diet with lutein, however, as of 2007, there appears to be no unequivocal evidence that lutein supplementation is necessary in eye healthcare despite its wide acceptance as a supplement. This may simply imply that supplementation with extra lutein is not necessary since it is a readily available xanthophyll in many vegetables. More recently trans-zeaxanthin and meso-zeaxanthin have also entered the marketplace as an eye healthcare supplements which indeed makes sense. However, is there yet a better carotenoid meeting all the requirements associated with eye/blood/brain barrier transport, accumulation in the macula and capable of long term use? The answer is found in the xanthophyll astaxanthin.

Dr. Mark Tso, at the Univ. of Ill, has demonstrated that astaxanthin is one such naturally occurring antioxidant meeting all of these critical criteria in rats. Astaxanthin is the carotenoid xanthophyll responsible for the red color in salmon, lobster, krill, crab, other shell fish and in the micro algae *Haematoccous pluvialis*. The latter source has made astaxanthin readily available worldwide for such uses. U.S. Pat. No. 5,527,533 was issued to the Univ. of Ill. describing the use of astaxanthin more fully in eye related diseases and which is hereby incorporated by in its entirety.

In addition, astaxanthin is a much more powerful antioxidant than canthoaxanthin, beta-carotene, zeaxanthin, lutein and alpha-tocopherol. Shimidzu et al. discovered that astaxanthin is 550 times more potent than alpha-tocopherol, 27.5 times more potent than lutein and 11 times more potent that beta-carotene in quenching singlet oxygen. In addition, Bagchi discovered that natural astaxanthin is 14 times more potent than alpha-tocopherol, 54 times more potent that beta-carotene and 65 times more potent that ascorbic acid (Vitamin C) in scavenging oxygen free radicals. Thus, though there are dramatic differences in the potency of astaxanthin when comparing the quenching of singlet oxygen and the scavenging of oxygen free radicals, it is clear that astaxanthin compares very favorably to zeaxanthin and lutein, the two carotenoids that are found naturally in the retina.

There is one more aspect of carotenoids, namely that some carotenoids can act as pro-oxidants. This is important since a carotenoid with pro-oxidant capability actually causes oxidation to occur in the body when high concentrations are present in tissue. Martin, et al. showed that beta-carotene, lycopene and zeaxanthin can become pro-oxidants under certain conditions, however because astaxanthin is the most potent of all carotenoids, Beutner et al. showed that astaxanthin can never be nor has it ever exhibited any pro-oxidant activity unlike the zeaxanthin found in the human eye. Since humans already have an abundant source of lutein and trans-zeaxanthin in their diets from many vegetable sources and are already present in the human eye, it appears that astaxanthin with its unique qualifying properties, unlike lutein or trans-zeaxanthin, may be the eye healthcare supplement of choice. With astaxanthin's extraordinarily potent antioxidant properties, its ability to cross the blood brain/eye barrier and concentrate in the retinal macula in other mammalian species, without the side effects seen with canthaxanthin, and in light of Tso's contributions, astaxanthin, in a convenient dietary supplement presentation, may emerge as the pre-eminent new ingredient addition to lutein and/or zeaxanthin eye healthcare supplementation for the management of eye related oxidative stress and thus the prevention and mitigation of degenerative diseases of the eye such as age related macular degeneration (ARMD) and cataract formation if astaxanthin deposition can be experimentally confirmed in human retinal tissue.

In addition, Tso found that light induced damage, photoreceptor cell damage, ganglion cell damage and damage to neurons of the inner retinal layers can be prevented or ameliorated by the use of astaxanthin including neuronal damage from ischemic, photic, inflammatory and degenerative insult in rats. Tso's patent claims the use of astaxanthin across a wide range of eye diseases including age related macular degeneration, diabetic neuropathy, cystoid macular edema, central retinal arterial and veneous occlusion, glaucoma and inflammatory eye diseases such as retinitis, uveitis, iritis, keratitis and scleritis, all disease states common to eye insult by oxidative species such as free radicals however this work was never confirmed in humans.

Oral administration of astaxanthin confirms that it is at least transported into human blood stream, however, its deposition in human retinal tissue has never been confirmed.

Astaxanthin is the major pigment of certain micro algae and crustaceans. Astaxanthin is a lipid-soluble pigment primarily used for pigmenting cultured fish, like salmon, which must ingest astaxanthin to yield consumer-acceptable pink-colored salmon muscle. Astaxanthin also is an antioxidant which is about 100 to about 1000 times more effective than alpha-tocopherol.

The prime source of commercial S,S'-astaxanthin is micro algae and, to a very small extent, is found in krill oil derived from *Euphasia superba* (Antarctic Krill). Astaxanthin also is available synthetically, however synthetic astaxanthin may not be safe for use in humans since it contains 3 known enantiomers including R,R', R, S' and S,S' which are not easily nor economically separated two of which have unknown human safety data. The preferred naturally-occurring S,S'-astaxanthin can be used in the composition and method of the present invention.

As previously stated, the retinal pigment epithelium protects the retina by providing a blood-retinal brain barrier. The barrier excludes plasma constituents that are potentially harmful to the retina. As also previously stated, the blood-retinal brain barrier only permits lutein and zeaxanthin to enter the retina, and excludes other carotenoids present in human serum, including beta-carotene which is the most abundant carotenoid in human serum. Astaxanthin is not a naturally-occurring constituent in the retina. Therefore, the presence of a physiologically significant amount of astaxanthin in the retina of rats may illustrate the ability of astaxanthin to readily cross the blood-retinal brain barrier into the retina of humans. The optimal dose of the composition can be determined by a person skilled in the art after considering factors such as the disease or injury to be treated, the severity of the central nervous system damage by oral administration.

The daily dose of composition can be administered daily or in accordance with a regimen determined by a person skilled in the art, with the length of treatment depending upon the severity and nature of the injury to the central nervous system, the need to improve accommodation or to control dry eye syndrome.

The composition can be administered to an individual orally. When administered orally, the composition, for example, can be in the form of a liquid preparation, The administration of the composition to an individual suffering from an eye injury or disease, such as free radical-induced injury, benefits the vision of the individual by preventing further photoreceptor cells from damage or destruction. The free radical-induced damage can be attributed to light-induced injury or to injury resulting from an ischemic insult and subsequent reperfusion or neurodegenerative diseases. The administration of astaxanthin also helps prevent and retard photic injury in addition to ameliorating photic injury.

The administration of the composition ameliorates photoreceptor cell damage that is light induced, and ameliorates ganglion cell damage that is induced by ischemic insult and subsequent reperfusion. The administration of astaxanthin also retards the progress of degenerative eye diseases and benefits the vision of individuals suffering from a degenerative eye disease, such as age-related macular degeneration.

The administration of the composition also provides a method of treating ischemic retinal diseases, such as diabetic retinopathy, cystoid macular edema, central retinal arterial occlusion, central retinal venous occlusion and glaucoma. In addition, the composition is useful in treating inflammatory diseases of the eye such as retinitis, uveitis, iritis, keratitis and scleritis wherein free radicals are produced in abundance, the prevention of cataracts and the treatment of certain causes of dry eye syndromes.

Therefore, the antioxidant properties of the composition, coupled with the ability of the composition to cross the blood-retinal brain barrier, admixed with anti-inflammatory sources of EPA and DHA and the lack of toxicity of the composition and the lack of adverse side effects associated with the composition, make the composition a useful composition to prevent or ameliorate such eye related diseases, dry eye syndrome and/or cataracts and dry eye syndromes.

"Reacted" Carotenoids and Delivery System

The analytical analysis of the product blend of krill oil and carotenoids, including astaxanthin during testing, gave conflicting recovery data for the added astaxanthin when evaluated using HPLC (High-Performance Liquid Chromatography, also known as High-Pressure Liquid Chromatography) analysis. It was determined that over time, astaxanthin apparently, and rapidly, chemically combined in what appears to be an unknown way with one or more krill oil components to produce a compound that is not detectable using the HPLC methodology used to quantify the amount of astaxanthin in such initially blended product. As a result, a "capsule in a capsule" was designed to prevent such loss of astaxanthin to the krill oil in order to retain label claims. This is an unexpected observation/result with great benefits. Further, it is believed that astaxanthin when mixed with pure fish oil containing essentially all triacylglycerides bound fatty acids, does not result in quantitative loss of astaxanthin to fish oil components as observed in krill oils. One skilled in the art would not have anticipated the instability of astaxanthin and other carotenoids in such added mixtures.

Testing has determined that astaxanthin added to krill oil results in an unstable product with respect to recoverable astaxanthin by HPLC analysis. A chemical reaction most likely takes place between krill oil and at least astaxanthin in such mixtures. Nevertheless, the astaxanthin does not seem to be destroyed in such mixtures since UV based analysis indicates that the astaxanthin moiety is still present without structural loss because it is still able to absorb UV at the appropriate quantifying absorption wavelength of astaxanthin at essentially 100% quantification of the amount of astaxanthin added to such blended product. Had UV alone been used to determine product stability the decrease in recoverable astaxanthin over time would not have been observed. The test results, tables and charts of FIGS. 2-6 show the decrease in recoverable astaxanthin over time.

The carotenoids admixed with krill oil should be able to address not only the eye diseases known to be ameliorated by carotenoids but also the inflammatory diseases of the eye (including but not limited to dry eye syndrome) associated with the known anti-inflammatory activity of omega-3's. Just because phospholipid bound EPA and DHA are active alone as an anti-hyperlipidemic or as a reducer of pain in arthritic joints does not insure that such phospholipids from any source such as krill oil would prove effective for the treatment of inflammatory conditions of the eye. The AREDS2 study cited above is an example. This study was designed to determine if triglyceride bound omega-3 fatty acids would be effective in amelioration of inflammatory eye diseases.

As noted before, the astaxanthin disappears and is converted to a new product in the presence of the krill oil. Other carotenoids can possibly have a similar effect. This is an unexpected result such that the addition of some carotenoids and primarily astaxanthin to krill oil results in the chemical reaction. The design of the capsule in a capsule prevents initial mixing.

In accordance with a non-limiting example, FIG. 1 illustrates a medicine or drug delivery system at 10 that includes a central capsule 12 containing carotenoids 13 while an outer capsule 14 contains krill oil 15 and contains the inner capsule as illustrated. This capsule within the capsule prevents the disappearance of the carotenoids and the inability of standard HPLC (high-performance liquid chromatography) methods to quantitatively recover the carotenoids, especially with astaxanthin. Both capsules 12,14 could be formed of gelatin or similar material and formed to prevent mixing of carotenoids and krill oil until after capsule ingestion.

When added alone or in combination with other carotenoids, astaxanthin HPLC based recovery quickly abates much to the surprise of those skilled in the art. There is possible trans-esterification occurring between krill oil fatty acid esters and partially esterified carotenoids that creates a new compound. It is possible that the compound could be EPA trans-esterified onto astaxanthin. Thus, to deliver the label amount of each carotenoid in a single dose, the krill oil and the carotenoids are not allowed to mix because of the incompatibility issue. FIG. 1 shows the technical solution using the capsule within a capsule in accordance with a non-limiting example.

FIG. 1 shows the medicine delivery system 10 that includes the inner capsule 12 containing mixed carotenoids in one example comprising at least S,S'-astaxanthin derived from *Haematococcus pluvialis* and one or more of lutein and/or trans-zeaxanthin or meso-zeaxanthin. The outer capsule 14 contains a therapeutically effective amount of krill oil comprising phospholipid bound and triglyceride bound EPA and DHA and the krill oil contains at least 30% total phospholipids.

In an example, 50-1,000 mg of krill oil can be contained in the outer capsule 14. In another example, the mixed carotenoids can include 0.5 to 8 mg of astaxanthin, 2 to 15 mg of lutein, and 0.2 to 12 mg of trans-zeaxanthin within the inner capsule. About 4 mg of astaxanthin, about 10 of lutein and about 1.2 mg of trans-zeaxanthin is contained within the inner capsule in one example. The use of this medicine delivery system 10 provides a new composition after ingestion in vivo that includes the therapeutically effective amount of synergistic multi-ingredient composition of krill oil containing phospholipid bound and triglyceride bound EPA and DHA in which the krill oil contains at least 30% total phospholipids and mixed carotenoids comprising at least S,S'-astaxanthin derived from *Haematococcus pluvialis* that has reacted with the krill oil, and one or more of lutein and/or trans-zeaxanthin or meso-zeaxanthin. This allows a method of treating an individual by administering the capsule that includes the therapeutically effective amount of a synergistic multi-ingredient composition of krill oil and carotenoids and reacting carotenoids in vivo with the krill oil after ingestion.

FIG. 2 is a chart showing data of astaxanthin at 13 days post formulation reacting with krill oil, but essentially neither lutein nor zeaxanthin. Astaxanthin is a keto-alcohol while lutein and zeaxanthin are alcohols and this can possibly make some difference. It should also be understood that the krill oil and "reacted" carotenoids, such as astaxanthin, and possibly zeaxanthin and lutein, lose their ability to be recovered over time from the mixture but can still be quantitated by ultraviolet (UV) analysis. For example, the chromophores of the carotenoids are not destroyed when the reaction takes place over time and can be used to develop a number of products useful for cardiovascular applications, joint health care applications, eye care and other diseases.

Referring now to the chart in FIG. 2, there are shown various samples and explanation. Sample 3/1 is a mixture of astaxanthin in krill oil only and showing a 23% reduction in HPLC recoverable astaxanthin by day 13 while retaining total carotenoid concentration as measured by UV analysis. Similar results were obtained in the presence of lutein, however the "loss" of recoverable lutein was minimal while astaxanthin provided the same loss as the 3/1 sample. Sample 5/1 is mixed carotenoids. In this example, there is essentially no loss of HPLC recoverable astaxanthin while there is minimal loss of lutein and zeaxanthin (probably within experimental error). Recoveries of lutein and zeaxanthin in the presence of krill oil were within experimental error. Recoveries of these same carotenoids without krill oil, however, were less than expected because lutein and zeaxanthin are not very soluble in astaxanthin oleoresin.

Admixture of astaxanthin derived from hp biomass extraction with krill oil above normal levels shows a continued loss of recoverable astaxanthin over day 1 concentrations while the total carotenoid concentration as measured by UV analysis remains essentially unchanged, indicating that a chemical reaction is taking place when relatively high concentrations of astaxanthin are added to krill oil. Further testing with LC/MS/MS can determine the resulting chemical species being formed. It is believed this "reaction" is unique to krill oil phospholipids but other experiments can be conducted with other chemical species to determine the scope of this reaction. Further determination can be made whether all keto-alcohols (e.g., astaxanthin) react, and alcohols, amines, etc. A full strength eye care composition product included 4 mg of astaxanthin, 10 mg lutein and 1.2 mg zeaxanthin in an inner capsule with krill oil in the outer capsule to prevent comingling of the carotenoids with krill oil and preserve label claims in the event of an HPLC analysis of a simple blended product.

FIG. 3 is another chart showing a stability analytical report for the astaxanthin, lutein and zeaxanthin with percent change from day 0 to day 12 at 20 degrees C. This is compared to FIG. 2 charts that show for day 13. The charts in FIG. 2 show the Aker Biomarine sample while the charts in FIG. 3 show use for an eye formula as claimed and also a FlexPro such as disclosed in commonly assigned U.S. patent application Ser. No. 12/840,372 and published as U.S. Patent Publication No. 2011/0020316 with the A corresponding to Aker Biomarine krill oil and E corresponding to Enzymotec krill oil.

FIG. 4 is a chart showing results for 50 degrees C. FIG. 5 is a chart showing summary of changes by UV as described above. FIG. 6 is another chart showing results with a day 26 added with the eye formulation as described.

Figure 7:
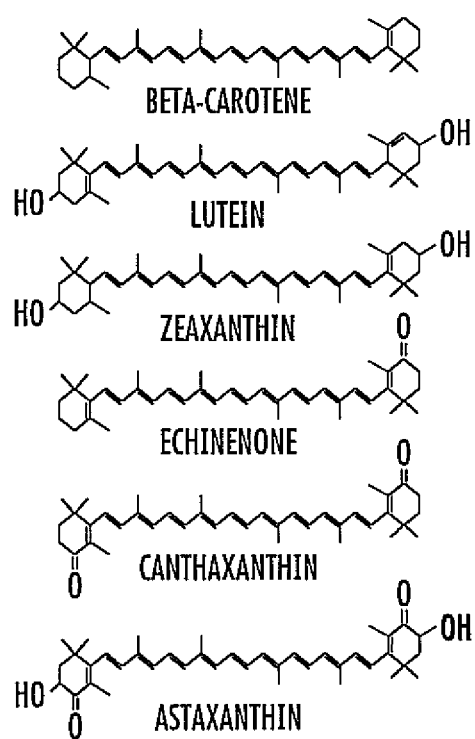
FIG. 7 are chemical formula of various carotenoids and showing the differences among them.

FIG. 7 shows the different chemical formula for different carotenoids. This indicates the differences and why krill oil can react more readily with one type of carotenoid and not others.

Many modifications and other embodiments of the invention will come to the mind of one skilled in the art having the benefit of the teachings presented in the foregoing descriptions and the associated drawings. Therefore, it is understood that the invention is not to be limited to the specific embodiments disclosed, and that modifications and embodiments are intended to be included within the scope of the appended claims.

That which is claimed is:

1. A method of treating in an individual a disorder of the eye selected from the group consisting of dry eye syndrome and macular degeneration by administrating in an oral single dosage capsule form a therapeutically effective amount of a dietary supplement composition comprising krill oil containing phospholipid bound and triglyceride bound EPA and DHA, the krill oil comprising at least 30 percent total phospholipids and wherein the krill oil is about 58 percent to about 99.5 percent by weight of the total composition, 3S,3'S-astaxanthin derived from *Haematococcus pluvialis* (Hp), lutein and trans-zeaxanthin, wherein the 3S, 3'S-astaxanthin derived from *Haematococcus pluvialis* (Hp) is 0.1 to 16 percent by weight of the krill oil, the lutein is 0.4 to 30 percent by weight of the krill oil, and the trans-zeaxanthin is 0.04 to 24 percent by weight of the krill oil, wherein the composition includes 50 to 500 mg of krill oil per daily dose in the oral single dosage capsule.

2. The method according to claim 1, further comprising administering 0.5 to 8 mg of astaxanthin, 2 to 15 mg of lutein and 0.2 to 12 mg of trans-zeaxanthin on a daily basis.

3. The method according to claim 2, further comprising administering about 4 mg of astaxanthin, about 10 mg of lutein and about 1.2 mg of trans-zeaxanthin.

4. A method of treating in an individual a disorder of the eye selected from the group consisting of dry eye syndrome and macular degeneration by administrating in an oral single dosage capsule form a therapeutically effective amount of a dietary supplement composition comprising krill oil containing phospholipid bound and triglyceride bound EPA and DHA, the krill oil comprising at least 30 percent total phospholipids and wherein the krill oil is about 77 percent to about 99.5 percent by weight of the total composition, 3S,3'S-astaxanthin derived from *Haematococcus pluvialis* (Hp), lutein and trans-zeaxanthin, wherein the 3S,3'S-astaxanthin derived from *Haematococcus pluvialis* (Hp) is about 0.8 to 8 percent by weight of the krill oil, the lutein is about 2.0 to 20 percent by weight of the krill oil, and the trans-zeaxanthin is about 0.24 to 2.4 percent by weight of the krill oil, wherein the composition includes 50 to 500 mg of krill oil per daily dose in the oral single dosage capsule.

5. The method according to claim 4, further comprising administering meso-zeaxanthin.

6. The method according to claim 5, further comprising administering 0.5 to 8 mg of astaxanthin, 2 to 15 mg of lutein and 0.2 to 12 mg of trans-zeaxanthin on a daily basis.

7. The method according to claim 6, further comprising administering about 4 mg of astaxanthin, about 10 mg of lutein and about 1.2 mg of trans-zeaxanthin.

\* \* \* \* \*